US012358895B2

(12) United States Patent
Mao et al.

(10) Patent No.: US 12,358,895 B2
(45) Date of Patent: Jul. 15, 2025

(54) PROCESS FOR MANUFACTURE OF (S)-N-(3-((2-((4-((1-ACETYLPYRROLIDIN-3-YL)(METHYL)AMINO)PHENYL)AMINO)-5-METHOXYPYRIMIDIN-4-YL)OXY)PHENYL) ACRYLAMIDE, AND FORMULATIONS THEREOF

(71) Applicants: ACEA Therapeutics, Inc., San Diego, CA (US); HANGZHOU ACEA PHARMACEUTICAL RESEARCH CO., LTD, Hangzhou (CN); ZHEJIANG ACEA PHARMACEUTICALS CO., LTD., Quzhou (CN)

(72) Inventors: Long Mao, San Diego, CA (US); Jia Liu, San Diego, CA (US); Yile Chen, Hangzhou (CN); Yuning Hua, Hangzhou (CN); Kunhua Dong, Hangzhou (CN); Liang Chen, Hangzhou (CN); Bojie Weng, Hangzhou (CN); Xiaopeng Mo, Hangzhou (CN); Kongen Dai, Hangzhou (CN); Yimei Bao, Hangzhou (CN); Jian Wu, Hangzhou (CN); Bin Liang, Hangzhou (CN); Guanglin Zhou, Hangzhou (CN); Zhen Wang, Hangzhou (CN)

(73) Assignee: ACEA Therapeutics, Inc., San Diego, CA (US)

( * ) Notice: Subject to any disclaimer, the term of this patent is extended or adjusted under 35 U.S.C. 154(b) by 768 days.

(21) Appl. No.: 17/266,075

(22) PCT Filed: Aug. 9, 2018

(86) PCT No.: PCT/CN2018/099535
§ 371 (c)(1),
(2) Date: Feb. 4, 2021

(87) PCT Pub. No.: WO2020/029156
PCT Pub. Date: Feb. 13, 2020

(65) Prior Publication Data
US 2021/0309642 A1    Oct. 7, 2021

(51) Int. Cl.
*C07D 403/12* (2006.01)
*A61K 9/20* (2006.01)
*A61K 9/28* (2006.01)
*A61K 9/48* (2006.01)

(52) U.S. Cl.
CPC .......... *C07D 403/12* (2013.01); *A61K 9/2095* (2013.01); *A61K 9/28* (2013.01); *A61K 9/4858* (2013.01); *A61K 9/4866* (2013.01); *C07B 2200/13* (2013.01)

(58) Field of Classification Search
CPC ...... C07D 403/12; A61K 9/2095; A61K 9/28; A61K 9/4858; A61K 9/4866; A61K 9/2054; A61K 31/506; C07B 2200/13; A61P 35/00
See application file for complete search history.

(56) References Cited

U.S. PATENT DOCUMENTS

| 9,464,089 B2 * | 10/2016 | Xu ...................... C07D 239/49 |
| 9,920,074 B2 | 3/2018 | Xu et al. |
| 10,562,918 B2 | 2/2020 | Xu et al. |

FOREIGN PATENT DOCUMENTS

| CN | 105916851 A * | 8/2016 | .......... A61K 31/506 |
| EP | 3019496 A2 | 5/2016 | |
| JP | 2016-528209 A | 9/2018 | |
| WO | 200915871 A1 | 12/2009 | |
| WO | 2015006754 A2 | 1/2015 | |

OTHER PUBLICATIONS

English translation of CN105916851A. (Year: 2016).*
Stahl et al., "Handbook of Pharmaceutical Salts Properties, Selection, and Use", Wiley-VCH, pp. 1-374. (Year: 2002).*
"Tartaric Acid", Technical Evaluation Report, 1-12. (Year: 2011).*
Extended European Search Report corresponding to European Patent Application No. 18929249.3, mailed Feb. 28, 2022, 7 pages.
International Search Report for international patent application PCT/CN2018099535 (WO2020029156), dated May 6, 2019, 4 pages.
Written Opinion of the International Searching Authority for international patent application PCT/CN2018099535 (WO2020029156), dated May 6, 2019, 4 pages.
International Preliminary Report on Patentability for international patent application PCT/CN2018099535 (WO2020029156), dated Feb. 9, 2021, 5 pages.
Communication pursuant to Rules 161(2) and 162 EPC for European patent application EP18929249.3, dated Mar. 26, 2021, 3 pages.
Claims for European patent application EP18929249.3, dated Sep. 29, 2021, 4 pages.
Claims(Marked-up) for European patent application EP18929249.3, dated Sep. 29, 2021, 8 pages.

(Continued)

*Primary Examiner* — Matthew P Coughlin
*Assistant Examiner* — Meghan C Heasley
(74) *Attorney, Agent, or Firm* — McNeill PLLC

(57) ABSTRACT

The invention relates to solid forms of certain N-(pyrimidinyloxy)acrylamide derivatives that are useful in the treatment of proliferation and immunological disorders and other diseases related to the dysregulation of kinases including EGFR (including HER), Alk, PDGFR, BLK, BMX/ETK, BTK, FLT3 (D835Y), ITK, JAK1, JAK2, JAK3, TEC and TXK. The invention provides methods of making these materials and their salts and polymorphs, and intermediates for preparing these materials, as well as pharmaceutical compositions comprising these materials. The solid forms and pharmaceutical compositions comprising them are useful to treat conditions including a proliferation disorder, a tumor, an inflammatory disease, an autoimmune disease, psoriasis, dry eye, rheumatoid arthritis, or lupus.

18 Claims, 12 Drawing Sheets

(56) References Cited

OTHER PUBLICATIONS

Response to Communication pursuant to Rules 161(2) and 162 EPC for European patent application EP18929249.3, dated Sep. 29, 2021, 2 pages.
Journal of Synthetic Organic Chemistry, Japan, 1990, 48(1), pp. 71-72 received from the Japanese Patent Office (translation attached).

* cited by examiner

PEAK: 204.61.5417
280.21.1929

PEAK: 268.61.0002

PROCESS FOR MANUFACTURE OF (S)-N-(3-((2-((4-((1-ACETYLPYRROLIDIN-3-YL)(METHYL)AMINO)PHENYL)AMINO)-5-METHOXYPYRIMIDIN-4-YL)OXY)PHENYL) ACRYLAMIDE, AND FORMULATIONS THEREOF

The present application is a U.S. national phase filing of International Patent Application Serial No. PCT/CN2018/099535, filed on Aug. 9, 2018, entitled "Process for Manufacture of (S)—N-(3-((2-((4-((1-acetylpyrrolidin-3-yl)(methyl)amino)phenyl)amino)-5-methoxypyrimidin-4-yl)oxy)phenyl)acrylamide, and Formulations Thereof," the disclosure of which is incorporated by reference in its entirety for all purposes.

TECHNICAL FIELD

This disclosure relates to solid forms of N-(pyrimidinophenyl)-acrylamide compounds that are useful for the treatment of proliferation disorders and immunological conditions related to the dysregulation of kinases such as, but not limited to, EGFR (including HER), Alk, PDGFR, BLK, BMX/ETK, BTK, FLT3 (D835Y), ITK, JAK1, JAK2, JAK3, TEC, and TXK. Further disclosed are methods of making and using the compounds and solid forms thereof. Also disclosed are certain salt forms and physical forms of said compounds, pharmaceutical compositions containing these compounds, and methods to use these compounds, solid forms, and pharmaceutical compositions to modulate kinase activities and to treat certain proliferative and immunological conditions.

BACKGROUND ART

Certain N-(pyrimidinophenyl)acrylamide compounds of general formula (I)

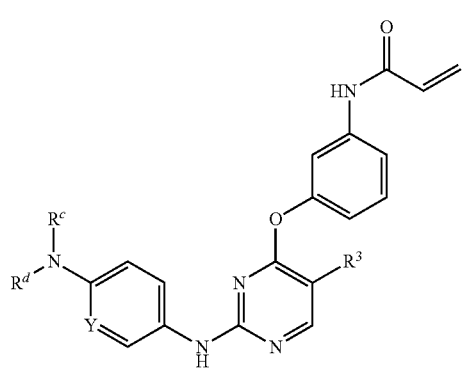

(I)

wherein $R^3$ can be alkoxy, $R^c$ can be alkyl, cycloalkyl, or heterocycloalkyl; Y can be N, CH, or C-halo; and $R^d$ can be H or alkyl;

have been described as potent modulators of certain protein kinases that are known to be important pharmaceutical targets. WO2015/0067654. These compounds are useful for treating certain protein kinase-mediated diseases, including cancer, immunological conditions, and chronic inflammation.

Of particular interest is the inhibition by compounds of Formula (I) of Bruton's Tyrosine Kinase (BTK), which plays a crucial role in maturation of B cells and activation of mast cells. Inhibitors of BTK are in clinical trials for B cell-related proliferative diseases (chronic lymphocytic leukemia, non-Hodgkin's Lymphoma) and autoimmune diseases such as X-linked agammaglobulinemia (XLA).

Certain compounds of general Formula (I), including Compound A

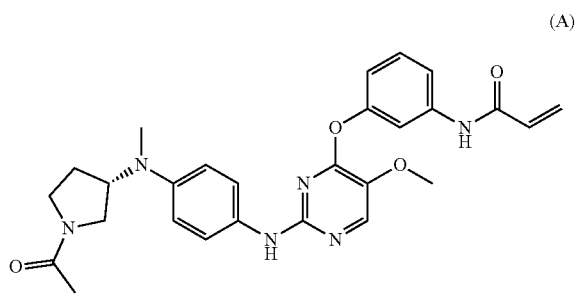

(A)

(S)—N-(3-(2-(4-((1-acetylpyrrolidin-3-yl)(methyl)amino)phenylamino)-5-methoxypyrimidin-4-yloxy)phenyl)acrylamide and pharmaceutically acceptable salts thereof, are of special interest due to their potent inhibition of protein kinases including EGFR and BTK, and are thus potentially suitable for clinical trials for treating EGFR- and/or BTK-associated conditions. In order to enhance their clinical utility, improved forms and formulations of these compounds were needed, and have now been developed.

An efficient method of making these compounds is needed to allow for clinical testing and commercial use. Such methods, and intermediates useful for the preparation of these compounds, are described herein. Certain salt forms and polymorphs of these compounds and methods for their preparation are also described.

In general, drug stability is an important consideration in the design, manufacture, and storage of pharmaceutical compositions. Drug products that lack stability can form degradation products that can cause undesirable side effects or, in some cases, can cause a decrease in the efficacy and bioavailability of the drug substance itself, making it difficult for physicians to prescribe consistent and effective doses. In order to develop Compound A for widespread pharmaceutical use, solid forms that can be produced consistently and in high purity are needed, as dosage forms and formulations of these solid forms that are stable for long-term storage. The invention provides such solid forms of Compound A as well as pharmaceutical compositions and treatment methods utilizing these solid forms.

SUMMARY

The present invention is directed to methods of preparing certain N-(pyrimidinyloxy)phenyl acrylamide compounds and solid forms thereof, and intermediates useful in their preparation. Also described are certain solid forms, salts and polymorphs of Compound A that are especially useful for development and manufacture of pharmaceutical products. Solid forms of Compound A that are especially useful, including a 1:1 salt of Compound A with L-(+)-tartaric acid (Compound A-TA) are described. Additionally, pharmaceutical compositions comprising these novel solid forms and methods for their preparation and use are described.

The disclosure provides a method of making Compound A

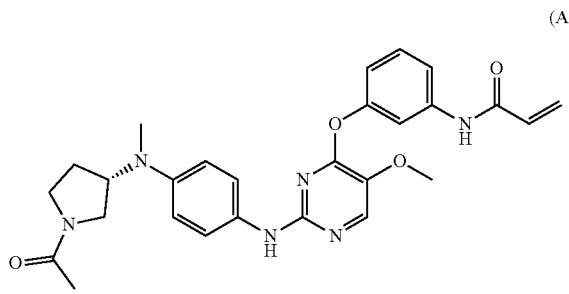

(A)

and a tartrate salt thereof, and a method for producing a novel solid form of the tartrate salt that can be consistently produced and is highly stable for formulation and storage. A stable polymorph of a salt of Compound A is also disclosed, along with methods of using the polymorph or other solid forms for preparation of pharmaceutical compositions and dosage forms.

Compound A is highly potent as a kinase inhibitor, but exhibits low water solubility which reduces its suitability for oral administration. The neutral compound, referred to as the free base of Compound A since it is weakly basic, is nearly insoluble at higher pH. In an effort to enhance water solubility, which is expected to greatly improve oral bioavailability, attempts were made to prepare acid addition salts of Compound A. Surprisingly, of twelve acids used in the initial testing [HCl, HBr, $H_3PO_4$, maleic acid, hydroxybutanedioic acid, citric acid, methanesulfonic acid, toluenesulfonic acid, camphorsulfonic acid, fumaric acid, L-(+)-tartaric acid, and D-(−)-tartaric acid], only (L)-(+)-tartaric acid produced a stable, crystalline solid. Therefore, the L-(+)-tartrate salt of Compound A, referred to hereinafter as Compound A L-(+)-tartrate, or Compound A-TA, is especially suited for development and is used in many of the compositions and methods herein.

In one aspect, the invention provides a solid form of Compound A:

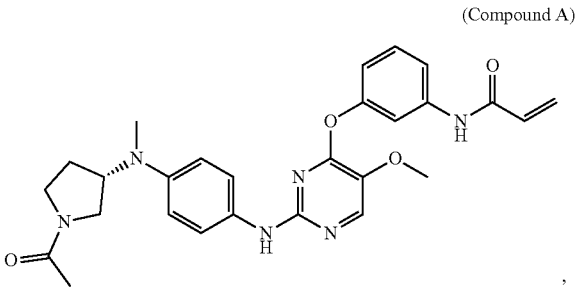 [SMILES: C=CC(=O)Nc1cccc(Oc2nc(Nc3ccc(N(C)[C@H]4CCN(C(C)=O)C4)cc3)ncc2OC)c1]

(Compound A)

, which is a tartrate salt. In some embodiments, it is a 1:1 salt of Compound A and L-(+)-tartaric acid. In some embodiments, it is a crystalline dihydrate.

In another aspect, the invention provides a stable and especially useful polymorph of the tartrate salt of Compound A, which is further described herein, and methods of preparing these salts.

The invention also provides pharmaceutical compositions containing the solid forms described herein, and methods of making highly stable drug product and dosage units using the pharmaceutical compositions. It provides dosage units in various forms, including capsules and tablets, with suitable quantities of the solid forms of Compound A and formulations thereof for treating conditions characterized by undesired levels of activity of EGFR and/or BTK.

In some embodiments, the pharmaceutical compositions of the invention are packaged with at least one protective agent, which can be one or more materials selected from desiccating agents, antioxidants, oxygen scavengers, and an inert gas. The protective agent(s) can reduce the rate of formation of traces of impurities when the pharmaceutical composition is exposed to heat or humidity or both.

The invention also provides dosage units comprising the pharmaceutical compounds of the invention and packed pharmaceutical products comprising these compounds.

In another aspect, the invention provides methods to use the compounds, solid forms, pharmaceutical compositions, and dosage units of the invention for treatment of a proliferation disorder, a cancer, a tumor, an inflammatory disease, psoriasis, dry eye, or an autoimmune disease, such as rheumatoid arthritis or lupus, in the subject. Exemplary proliferation disorders for treatment include sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer. Of special interest are B-cell related forms of lymphoma or leukemia, such as chronic myeloid leukemia and chronic lymphocytic leukemia.

The invention also provides improved methods to synthesize compounds such as Compound A or a pharmaceutically acceptable salt thereof.

Other aspects and advantages of the invention will be apparent from the embodiments and examples provided herein.

For the sake of brevity, the disclosures of the publications cited in this specification, including patents, are herein incorporated by reference.

DETAILED DESCRIPTION

Figure 1:
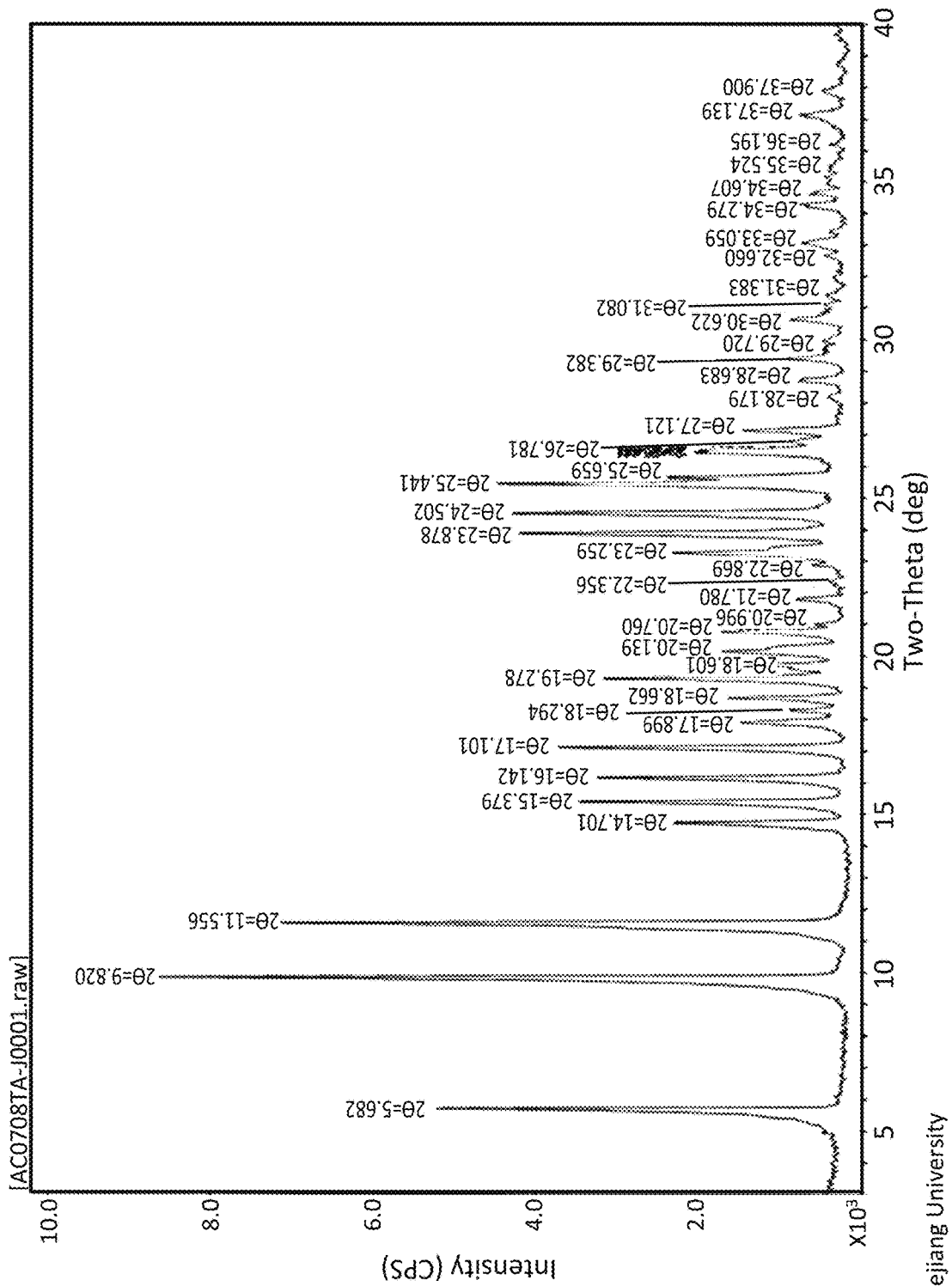
FIG. 1 is an X-ray powder diffraction pattern of polymorph Form I of Compound A-TA.
Figure 2:
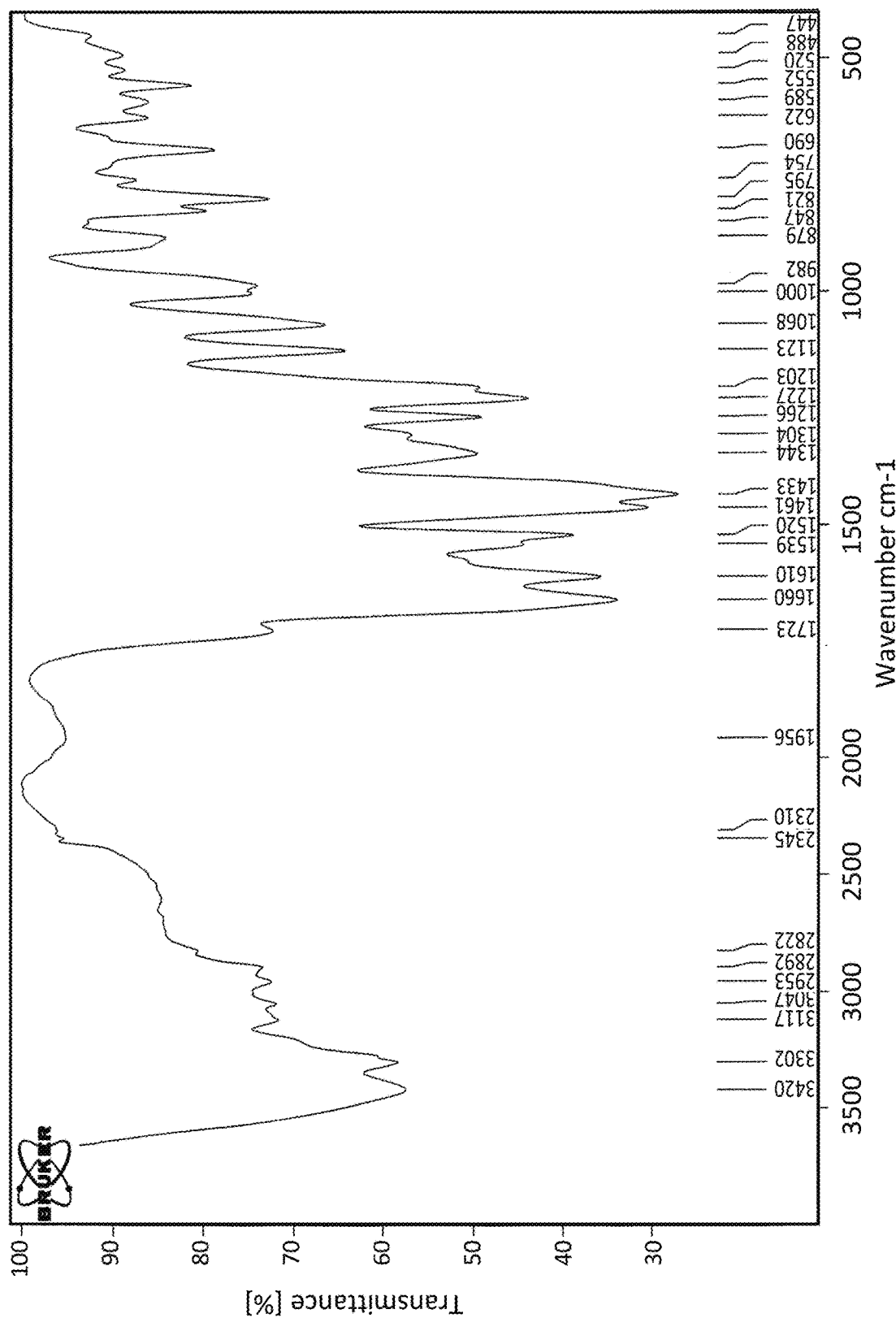
FIG. 2 is an Infrared spectrum of Compound A-TA.
Figure 3:
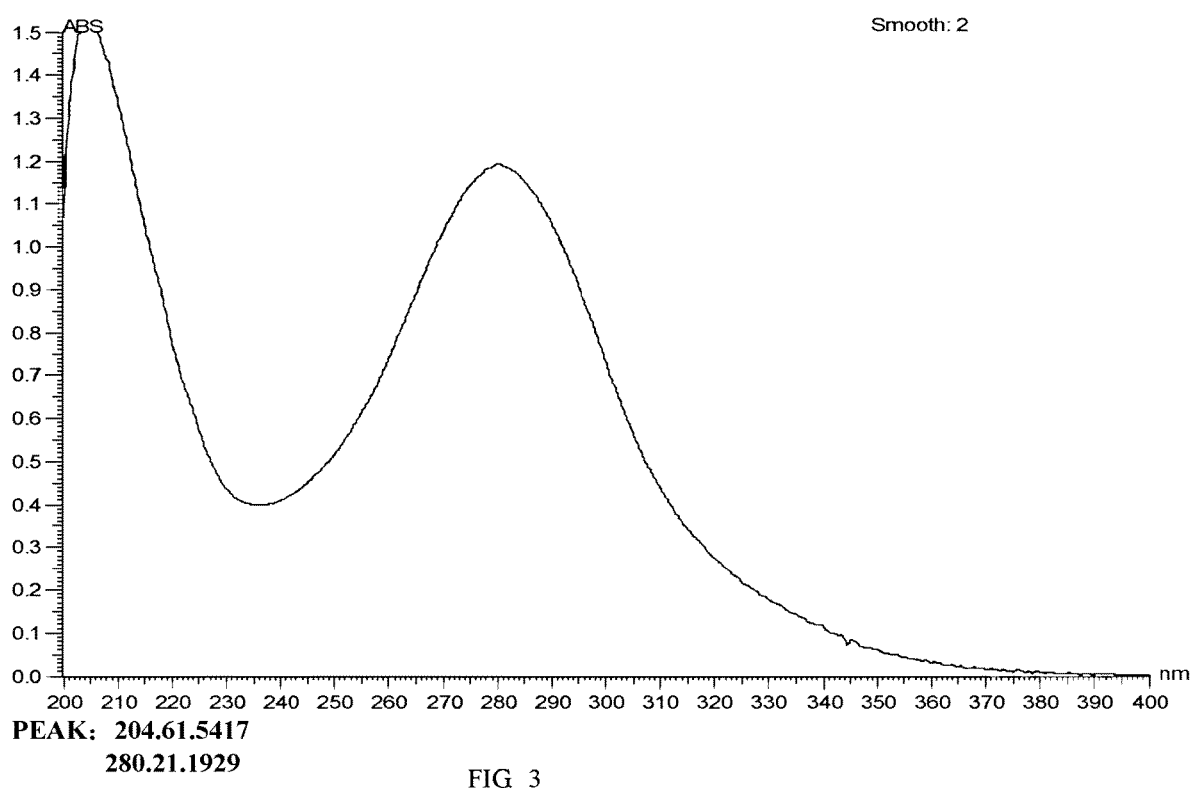
FIG. 3 shows an Ultraviolet spectrum of Compound A-TA in methanol.

The present invention encompasses improved methods of making certain N-(pyrimidinyloxy)phenyl acrylamide derivatives, which are useful in pharmaceutical compositions and in methods of treating certain proliferative disorders and immunological disorders. General methods for making compounds or precursors relevant to the invention as well as biochemical and biological data relevant to the invention can be found in WO2015/0067654 and U.S. Pat. No. 9,464,089.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

To provide a more concise description, some of the quantitative expressions given herein are not qualified with the term "about". It is understood that, whether the term "about" is used explicitly or not, every quantity given herein is meant to refer to the actual given value, and it is also meant to include to the approximation to such given value that would reasonably be inferred based on the ordinary skill in the art, including equivalents and approximations due to the experimental and/or measurement conditions for such given value. For example, when peaks in an XRPD are described as 'about' a specific value, the value includes a range of ±0.2°. Amounts of a material indicated in a claim are understood to include a range at least allowing for reasonable variations associated with the precision normally achieved in the context, and if not otherwise specified should normally be interpreted to include a range of ±10% around the specified value. Where a temperature is specified for a DSC, it should be understood to include a range of ±3° C.

Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002; Smith and March, March's Advanced Organic Chemistry: Reactions, Mechanisms, and Structure, Fifth Edition, Wiley-Interscience, 2001.

As used herein, the terms "including," "containing," and "comprising" are used in their open, non-limiting sense. Where an embodiment is described as 'comprising' specified substances, steps, or features, it is understood that the invention also includes corresponding embodiments 'consisting essentially of' and 'consisting of' the same substances, steps or features.

It should be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —$NH_2$ group, or a mono- or dialkylamino group.

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

The term "acyl" refers to a group R—C(O)— where R is from 1 to 10 carbon atoms ($C_{1-10}$) of a straight, branched, or cyclic configuration or a combination thereof, attached to the parent structure through carbonyl functionality. Such R group may be saturated or unsaturated, and aliphatic or aromatic.

The term "cyano" refers to the group —CN.
The term "nitro" refers to the group —$NO_2$.
The term "hydroxyl" refers to the group —OH.

Those skilled in the art will recognize that the species listed or illustrated above are not exhaustive, and that additional species within the scope of these defined terms may also be selected.

Any formula depicted herein is intended to represent each compound that is not inconsistent with the depicted structural formula. For example, a formula given herein that does not expressly describe the stereochemistry at one or more chiral centers is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Compound structures and names depicted herein as a specific enantiomer refer to the enantiomer designated. It is understood that such compounds may nonetheless contain small amounts, i.e. less than 10% and typically less than 5%, of the opposite enantiomer.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically-labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically-labeled compounds of the embodiments and prodrugs thereof can generally be prepared by carrying out the procedures disclosed in the schemes or in the examples and preparations described below by substituting a readily available isotopically-labeled reagent for a non-isotopically-labeled reagent.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

Representative Embodiments

The following enumerated embodiments represent some aspects of the invention.

1. A solid form of Compound A:

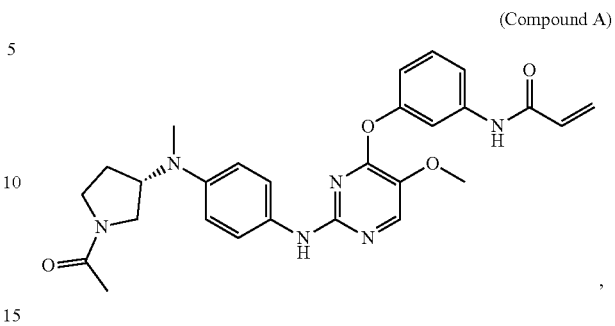

(Compound A)

which is a tartrate salt.

2. The solid form of embodiment 1, which is a 1:1 salt of Compound A and L-(+)-tartaric acid.

3. The solid form of embodiment 1 or 2 that is a hydrate of the L-(+)-tartrate salt of Compound A.

4. The solid form of embodiment 3, which is a dihydrate.

5. The solid form of any one of the preceding embodiments, which is crystalline.

6. The solid form of any one of the preceding embodiments, which is a crystalline form having an X-ray powder diffraction pattern which comprises at least two peaks selected from: about 5.7°, about 9.8°, about 11.6°, about 14.7°, about 15.4°, about 16.1°, about 17.1°, about 19.3°, about 23.8°, about 24.5°, and about 25.4°, in terms of 2-theta.

7. The solid form of embodiment 6, wherein the X-ray powder diffraction pattern comprises at least three peaks, or at least four peaks, or at least five peaks, or at least six peaks, or at least seven peaks, or at least eight peaks, or at least nine peaks, or at least ten peaks, wherein the peaks are selected from: about 5.7°, about 9.8°, about 11.6°, about 14.7°, about 15.4°, about 16.1°, about 17.1°, about 19.3°, about 23.8°, about 24.5°, and about 25.4°, in terms of 2-theta. In a particular example, the XRPD pattern substantially matches the XRPD in FIG. 1.

8. The solid form of any one of the preceding embodiments, having a differential scanning calorimetry (DSC) thermogram comprising an endothermic peak at about 74° C.

Figure 7:
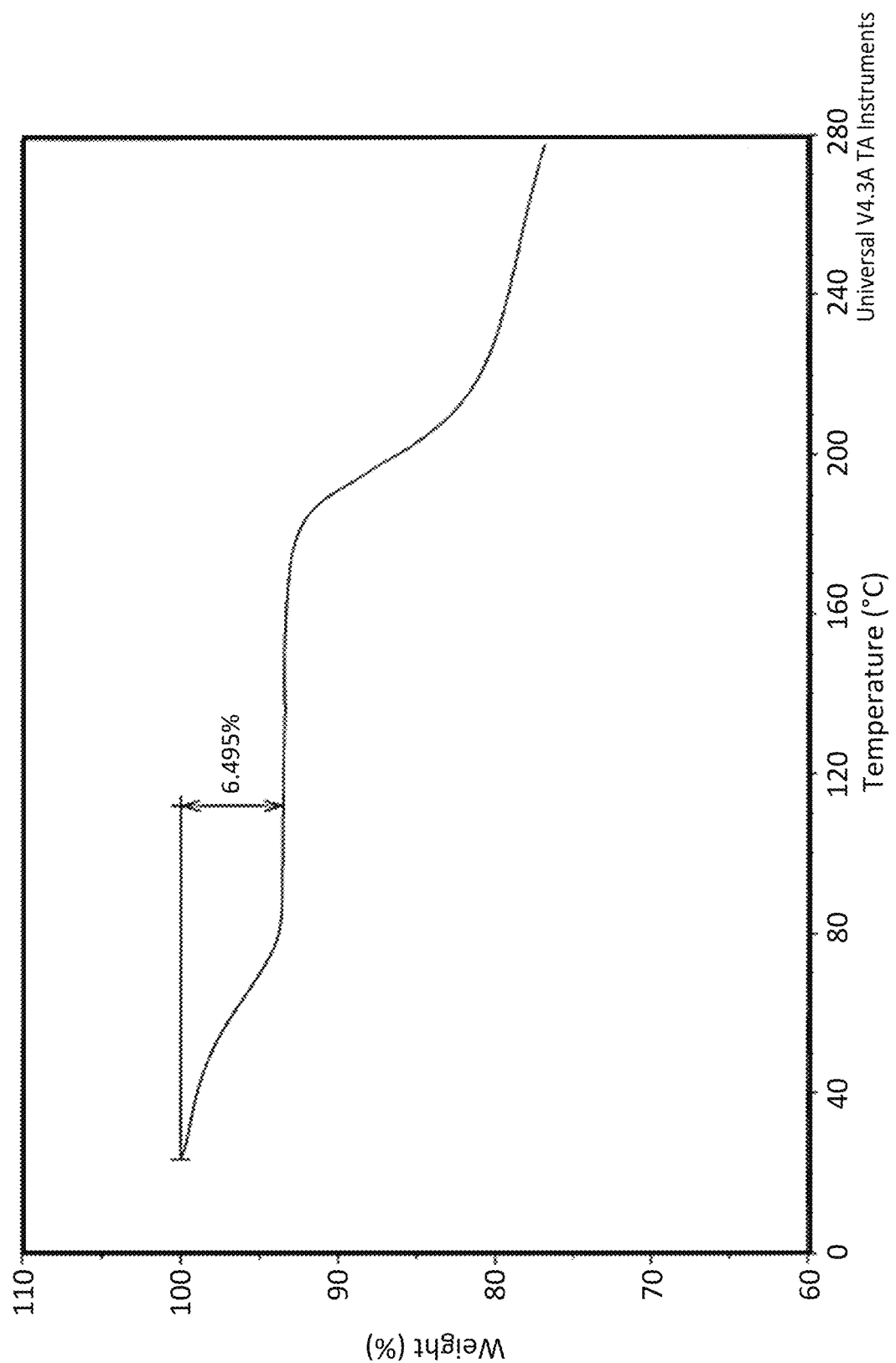
FIG. 7 shows a thermogravimetric analysis of polymorph Form I of Compound A-TA.

9. The solid form of any one of the preceding embodiments, having a thermogravimetric analysis (TGA) substantially as shown in FIG. 7.

10. A pharmaceutical composition comprising the solid form of Compound A according to any one of the preceding embodiments, admixed with at least one pharmaceutically acceptable excipient.

11. The pharmaceutical composition of embodiment 10, which comprises at least two pharmaceutically acceptable excipients.

12. The pharmaceutical composition of embodiment 10 or 11, comprising at least one pharmaceutically acceptable excipient selected from filler, a disintegrant, a glidant, an adhesive, a lubricant, and an antioxidant such as sodium bisulfite, sodium sulfite, sodium thiosulfate, butylated hydroxy toluene (antioxidant-264), butylated hydroxy anisole, citric acid, and vitamin E.

13. The pharmaceutical composition of embodiment 12, which comprises at least one pharmaceutically acceptable excipient selected from the group consisting of microcrystalline cellulose, croscarmellose sodium, mannitol, polyvinylpyrrolidone (PVP), and sodium stearyl fumarate. In some embodiments, the microcrystalline cellulose comprises, or consists of, a silicified microcrystalline cellulose such as silicified microcrystalline cellulose 50 (SMCC50) and/or silicified microcrystalline cellulose 90 (SMCC90).

14. A dosage unit comprising a solid form of Compound A according to any one of embodiments 1-9, in an amount equivalent to a weight of the free base of Compound A, selected from 25 mg, 50 mg, 75 mg, 100 mg, 150 mg, 200 mg, 250 mg, 300 mg, and 400 mg.

15. The dosage unit of embodiment 14, which is a tablet or a capsule.

16. The dosage unit of embodiment 14 or claim 15, which comprises Compound A-TA and one or more pharmaceutically acceptable excipients.

17. The dosage unit of embodiment 16, wherein the one or more pharmaceutically acceptable excipients comprise one or more excipients selected from the group consisting of microcrystalline cellulose, croscarmellose sodium, mannitol, polyvinylpyrrolidone (PVP), and sodium stearyl fumarate.

18. The dosage unit of any of embodiments 14-17, which comprises at least one pharmaceutically acceptable excipient selected from silicified microcrystallinecellulose 50, silicified microcrystallinecellulose 90, pregelatinized starch, mannitol, croscarmellose sodium, povidone, and sodium stearyl fumarate.

19. The dosage unit of any one of embodiments 14-18, which comprises an antioxidant such as sodium bisulfite, sodium sulfite, sodium thiosulfate, butylated hydroxy toluene (antioxidant-264), butylated hydroxy anisole, citric acid, and vitamin E.

20. A packaged pharmaceutical product, which comprises a pharmaceutical composition comprising Compound A and a protective agent as two separate materials in a closed container.

21. The packaged pharmaceutical product of embodiment 20, wherein the pharmaceutical composition comprises a dosage unit according to any of embodiments 14-18.

22. The packaged pharmaceutical product according to any one of embodiments 21-22, wherein the protective agent comprises at least one material selected from desiccating agents, antioxidants, oxygen scavengers, and an inert gas.

23. The packaged pharmaceutical product according to any one of embodiments 20-22, wherein the protective agent comprises at least one material selected from molecular sieve, silica gel, and a fiber desiccant.

24. The packaged pharmaceutical product according to any one of embodiments 20-23, wherein the protective agent and the pharmaceutical composition are contained in an airtight receptacle.

25. The packaged pharmaceutical product of embodiment 24, wherein the airtight receptacle is a sealed bottle.

26. A method to prepare a pharmaceutical composition according to any one of embodiments 10-13, which comprises combining the L-(+)-tartrate salt of Compound A with at least one pharmaceutically acceptable excipient.

27. The method of embodiment 26, wherein the at least one pharmaceutically acceptable excipient comprises a filler, which is optionally selected from mannitol and microcrystalline cellulose.

28. The method of embodiment 26 or 27, wherein the at least one pharmaceutically acceptable excipient comprises a disintegrant, which optionally comprises croscarmellose sodium.

29. The method of any one of embodiments 26-28, wherein the at least one pharmaceutically acceptable excipient comprises an adhesive, which is optionally polyvinylpyrrolidone (PVP).

30. The method of any one of embodiments 26-29, wherein the at least one pharmaceutically acceptable excipient comprises a lubricant, which is optionally sodium stearyl fumarate.

31. The method of embodiment 26, which comprises combining the L-(+)-tartrate salt of Compound A with microcrystalline cellulose, sodium stearyl fumarate, and PVP, and optionally mannitol, to form a mixture.

32. The method of embodiment 31, which comprises combining the L-(+)-tartrate salt of Compound A with microcrystalline cellulose, sodium stearyl fumarate, and PVP, and optionally mannitol, to form a mixture, and adding PVP and optionally water to form a wet granular mixture.

33. A pharmaceutical composition comprising Compound A-TA, which is prepared by the method of embodiment 26.

34. The method of embodiment 31 or embodiment 32, wherein the mixture is blended in a wet granulator.

35. A process for preparation of the L-(+)-tartaric acid salt of Compound A, which comprises contacting Compound A with L-(+)-tartaric acid in the presence of a solvent.

36. A process for preparing a solid form of Compound A, which comprises contacting Compound A with tartaric acid in a solvent.

37. The process of embodiment 36, which comprises contacting Compound A with L-(+)-tartaric acid in the presence of a solvent under conditions where the L-(+)-tartaric acid salt of Compound A precipitates as a solid from the solvent.

38. The process of embodiment 37, wherein the solvent comprises water and an organic co-solvent.

39. The process of embodiment 38, wherein the organic co-solvent is selected from acetone, isopropanol, ethanol, and tetrahydrofuran.

40. The process of embodiment 39, wherein the solid form of Compound A comprises Form I of the L-(+)-tartaric acid salt of Compound A.

41. A process to synthesize Compound A or a pharmaceutically acceptable salt thereof, which comprises reductive hydrogenation of Compound 1 to provide Compound 2:

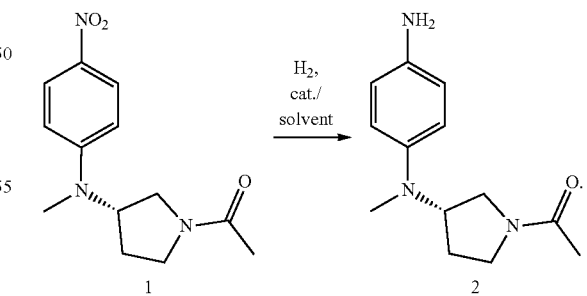

In this embodiment, the catalyst typically comprises palladium, platinum, or nickel. Suitably, the catalyst can be a palladium catalyst, optionally on a carbon support.

42. The process of embodiment 41, which further comprises allowing compound 2 to react with compound 3 to provide Compound A:

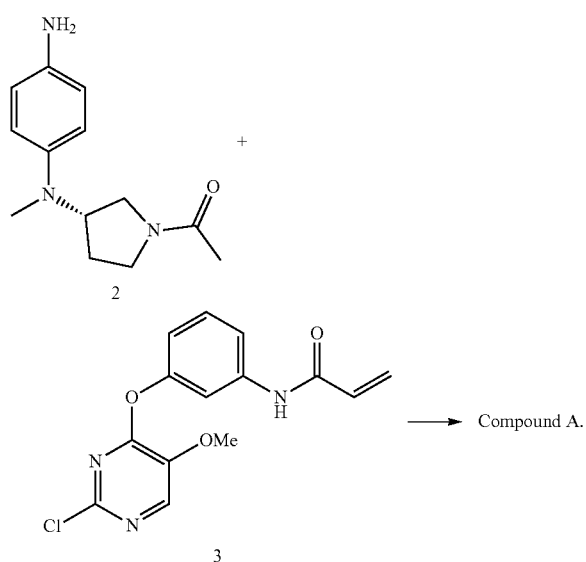

→ Compound A.

43. The method of embodiment 42, which further comprises contacting Compound A with L-(+)-tartaric acid to provide the L-(+)-tartaric acid salt of Compound A.

44. A method to treat an immunological disorder or a cell proliferation disorder, wherein the comprises administering to a subject in need thereof a solid form of Compound A according to any one of embodiments 1-9 or a pharmaceutical composition thereof.

In embodiment 12, the pharmaceutical composition can comprise one or more excipients selected from a filler, a disintegrant, an adhesive, a lubricant, and an antioxidant. Some examples of embodiment 12 comprise a filler, which can be selected from mannitol, dextrose, and a microcrystalline cellulose. In some such embodiments, the pharmaceutical composition comprises about 50-80% filler by weight. In one of these embodiments, the filler is a mixture of mannitol and microcrystalline cellulose. Some examples of embodiment 12 comprise a disintegrant, which can be croscarmellose sodium. In some such embodiments, the pharmaceutical composition comprises about 1-8% disintegrant by weight, and in a preferred embodiment it comprises 2-5% by weight disintegrant. Some examples of embodiment 12 comprise a lubricant, which can be selected from salts of stearic acid and salts of stearyl fumarate, particularly sodium stearyl fumarate. In some such embodiments, the pharmaceutical composition comprises about 0.5 to 2% lubricant by weight. In one of these embodiments, the lubricant is sodium stearyl fumarate. Some examples of embodiment 12 comprise an adhesive, which can be PVP or cross-linked PVP. In some such embodiments, the pharmaceutical composition comprises about 0-5% adhesive by weight. In one of these embodiments, the adhesive is Povidone K30 and the pharmaceutical composition comprises about 3% adhesive by weight. Compositions comprising the ratio (wt-%) of materials listed in Table 4 are a preferred embodiment. Compositions comprising the ratio (wt-%) of materials in the formulated material listed in Table 5 are another preferred embodiment. These preferred embodiments include compositions wherein the amount of any of the listed materials from Table 4 or 5 is within ±10% of the specified value.

In embodiments 26 to 32, the method to prepare a pharmaceutical composition can be a wet granulation process. In certain of these embodiments, the pharmaceutical composition comprises about 35% Compound A-TA, about 25% mannitol 25C, about 30% microcrystalline cellulose, about 5% croscarmellose sodium, about 3% PVP, and about 2% sodium stearyl fumarate, expressed as % by weight of the composition. 'About' in this embodiment means the percentage by weight of each of the components is the specified wt-% plus or minus 1 wt-%. In certain embodiments, the method of any one of embodiments 26 to 32 is performed using the ratios of materials, expressed in wt-%, in the formulations above, and preferably using the ratio of materials in either Table 4 or Table 5, where each listed proportion can optionally vary from the listed value by up to ±10% of the specified value. In a particular example, the process of any one of embodiments 26-32 comprises the following steps:

(a) Combine Compound A-TA, mannitol 25C, microcrystalline cellulose, and a fraction of the croscarmellose sodium to form a first mixture;
(b) Mix the first mixture in a wet granulator;
(c) Add PVP dissolved in water to form a second mixture and mix in the wet granulator;
(d) Dry the second mixture to provide a third mixture;
(e) Add the remainder of the croscarmellose sodium and the sodium stearyl fumarate to the third mixture and mix to form a final mixture. The final mixture is suitable to fill capsules to form a dosage unit of the invention.

Preferred embodiments of the method of embodiment 26 are presented in Examples 9 and 10, using the materials listed in Table 4.

In some embodiments, the solid form of Compound A-TA is a crystalline polymorph of Form I. Form I is characterized by an XRPD spectrum comprising one or more peaks at 2θ values (within the error range of the experiment) selected from the group consisting of: about 5.7°, about 9.8°, about 11.6°, about 14.7°, about 15.4°, about 16.1°, about 17.1°, about 19.3°, about 23.8°, about 24.5°, and about 25.4°. In some embodiments, Form I is characterized by one, two, three, four, five, six, seven, eight, nine, or 10, or more peaks selected from those specifically listed or within the error range of those listed. In some embodiments, Form I is characterized by the XRPD pattern substantially corresponding to the XRPD pattern in FIG. 1. The peaks may be described as 'about' a specified value in view of ordinary experimental variations, and the variation included may be ±0.2 2θ, or ±0.1 2θ.

In some embodiments, Form I of the L-(+)-tartrate salt of Compound A-TA is crystallized from a mixture of ethanol and water, or from a mixture of propanol and water, or from a mixture of methanol and water, or from a mixture of acetone and water. In some embodiments, Form I is crystallized from ethanol/water at a ratio of 1:1 to 9:1 (v/v). In some embodiments, the ethanol/water ratio is 1:1, or is 4:6, or is 9:1. In some embodiments, Form I is crystallized from methanol/water at a ratio of 7:3 (v/v). In some embodiments, Form I is crystallized from acetone/water at a ratio of 1:1, or 4:6, or 9:1.

Pharmaceutical Compositions

In one aspect, the invention provides pharmaceutical compositions and dosage units for oral administration. Aside from the pharmacological activity of an active pharmaceutical ingredient (API), several physical or physicochemical characteristics of the active substance are relevant for the preparation of solid oral dosage forms (including oral powders, granules, pellets, tablets, capsules, chewable tablets, dispersible tables, troches or lozenges). To achieve adequate formulation characteristics, such as correct assay, content, and mass uniformity, chemical and physical stability of the drug product, and a proper dissolution rate, the characteristics of the drug product intermediates also have to support a robust manufacturing process.

Therefore, in some aspects, how to achieve suitable adequate formulation characteristics depends on making and manufacturing process for stable pharmaceutical compositions containing a solid form of Compound A or a pharmaceutically acceptable salt thereof, or a pharmaceutically acceptable salt thereof.

In some embodiments, the pharmaceutical compositions described herein demonstrate high stability of the solid form of Compound A, or a pharmaceutically acceptable salt thereof, upon storage or under stability testing conditions described herein.

In some embodiments, the present invention also relates to methods of making the pharmaceutical compositions. Such methods may comprise a wet granulation process. In some embodiments, the wet granulation process includes the following steps:
  (a) Combine Compound A-TA, mannitol 25C, microcrystalline cellulose, and a fraction of the croscarmellose sodium (e.g., 80% of the indicated total amount of this material) to form a first mixture;
  (b) Mix the first mixture in a wet granulator;
  (c) Add PVP dissolved in water to form a second mixture, and mix in the wet granulator;
  (d) Dry the second mixture to provide a third mixture, and optionally mill this mixture in a comil; and
  (e) Add the remainder of the croscarmellose sodium and the sodium stearyl fumarate to the third mixture and mix to form a final mixture. The final mixture is suitable to fill capsules to form a dosage unit of the invention.

In some embodiments, the present pharmaceutical compositions may include pharmaceutically acceptable additive (s) into any suitable type of unit dosage form. Thus, in some embodiments, the pharmaceutical composition further comprises at least one pharmaceutically acceptable additive. Suitable additives include, but are not limited to, diluents, binders, vehicles, carriers, excipients, binders, disintegrating agents, lubricants, swelling agents, solubilizing agents, wicking agents, cooling agents, preservatives, stabilizers, sweeteners, flavors, and polymers. While any pharmaceutically acceptable additive is contemplated by the present disclosure, it should be understood that the additives selected for compounding with Compound A, or a pharmaceutically acceptable salt thereof, should not defeat the stability objectives of the present disclosure.

Examples of disintegrating agents include, but are not limited to, cross-linked sodium carboxymethylcellulose, croscarmellose sodium (e.g., VIVASOL®), crospovidone, and their mixtures. In some embodiments, the pharmaceutical composition comprises from about 0.1% (w/w) to about 10% (w/w), or about 5% (w/w), of croscarmellose sodium (e.g., VIVASOL®).

Examples of lubricating agents include, but are not limited to, magnesium stearate, stearic acid or a pharmaceutically acceptable alkali metal salt thereof, sodium stearyl fumarate, polyethylene glycol (such as Macrogol 6000) (particularly in granule or flake formulations to reduce friction with the mold), glyceryl behenate, talc, colloidal or fumed silicon dioxide and silica derivatives (such as Cab-O-Sil, Syloid® products, and the like), calcium stearate, sodium stearate, sodium lauryl sulfate, sodium chloride, magnesium lauryl sulfate, talc, and their mixtures. A portion of the lubricant may be used as an internal solid lubricant which is blended and granulated with other components of the granulation. Another portion of the lubricant may be added into the final blended material just before compression or encapsulation that coats the outside of the granules in the final formulation. In some embodiments, the pharmaceutical composition further comprises a disintegrating agent and a lubricant. In some embodiments, the lubricant is sodium stearyl fumarate. In some embodiments, the pharmaceutical composition comprises from about 0.05% (w/w) to about 5% (w/w) of sodium stearyl fumarate.

Oral pharmaceutical compositions as described herein can generally be in the form of individualized or multi-unit doses, such as tablets, caplets, powders, suspension tablets, chewable tablets, rapid melt tablets, capsules, e.g., a single- or double-shell gelatin capsule, tablet-filled capsules, effervescent powders, effervescent tablets, pellets, granules, liquids, solutions, or suspensions, respectively. In some embodiments, the pharmaceutical composition is formulated as an oral dosage form, or as a solid oral dosage form. In some embodiments, the oral dosage form is an oral powder, a granule, a pellet, a tablet, a capsule, a troch or a lozenge. In some embodiments, the tablet is a chewable tablet, a dispersible tablet, or a troch. In some embodiments, the pharmaceutical composition is formulated to contain a single dose or multiple doses. In some embodiments, each pharmaceutical composition dosage form (e.g., each tablet or capsule) comprises 25 mg, or 50 mg, or 100 mg, or 150 mg, or 200 mg, or 250 mg, or 300 mg, or 350 mg, or 400 mg, or 450 mg, or 500 mg free base equivalent of the Compound A. In some embodiments, the active ingredient (e.g., Compound A, or a pharmaceutically acceptable salt thereof such as Compound A-TA) is present in the pharmaceutical composition at a concentration of about 10 to about 70% (w/w), or about 15 to about 60% (w/w), or about 20% (w/w) to about 50% (w/w), or about 30-40% (w/w). For salt forms, the concentration is stated as the free base equivalent of the salt form.

While the solid forms of Compound A-TA disclosed exhibit high chemical and polymorphic stability, pharmaceutical compositions containing Compound A or Compound A-TA can be subject to oxidation under prolonged storage conditions, in the presence of humidity and/or oxygen. Data on the stability of selected pharmaceutical compositions of Compound A-TA are provided in the following Table, which shows slow formation of Impurity B, an oxidation product, during storage at elevated temperatures, and a reduced rate of formation of this impurity when an oxygen scavenger (PharmaKeep® CD20, also referred to as Deoxidizer CD20).

TABLE 1

Comparison Of Impurity Profile Between the Formulation of Table 4 (infra) and the Formulation of Table 5 (infra) when stored with and without an oxygen scavenger

| FORMULA 5 + NO DEOXIDIZER | RRT | 0 DAY (%) | 10 DAY/ 60° C. (%) | 1M-60° C. (%) | 1M-40° C. (%) | 2M-40° C. (%) | 3M-40° C. (%) | 6M-40° C. (%) |
|---|---|---|---|---|---|---|---|---|

TABLE 1-continued

Comparison Of Impurity Profile Between the Formulation of Table 4 (infra) and the Formulation of Table 5 (infra) when stored with and without an oxygen scavenger

| | RRT | 0 DAY (%) | 10 DAY-60° C. (%) | 1M-60° C. (%) | 1M-40° C. (%) | 2M-40° C. (%) | 3M-40° C. (%) | 6M-40° C. (%) |
|---|---|---|---|---|---|---|---|---|
| Impurity B (Oxidized) | 0.82 | 0.48 | 0.51 | / | 0.54 | 0.56 | 0.59 | 0.75 |
| Total Impurity | | 2.37 | 2.52 | / | 2.22 | 2.18 | 2.27 | 2.42 |
| Formula 4 + no Deoxidizer | RRT | 0 DAY (%) | 10 DAY-60° C. (%) | 1M-60° C. (%) | 1M-40° C. (%) | 2M-40° C. (%) | 3M-40° C. (%) | 6M-40° C. (%) |
| Impurity B (Oxidized) | 0.82 | 0.43 | 0.57 | 0.8 | 0.53 | 0.57 | 0.61 | 0.69 |
| Total Impurity | | 1.92 | 2.14 | 2.55 | 2.26 | 2.2 | 2.25 | 2.47 |
| Formula 4 + Deoxidizer CD20 | RRT | 0 DAY (%) | 10 DAY-60° C. (%) | 1M-60° C. (%) | 1M-40° C./ (%) | 2M-40° C./ (%) | 3M-40° C./ (%) | 6M-40° C./ (%) |
| Impurity B (Oxidized) | 0.82 | 0.43 | 0.46 | 0.55 | 0.49 | 0.52 | 0.5 | 0.45 |
| Total Impurity | | 1.92 | 2.01 | 2.37 | 2.23 | 2.19 | 2.2 | 2.22 |

*The same batch of Compound A-TA was used for both of the formulations whose stability is being compared in Table 1.

Formula 4 in Table 1 refers to formulated material that was made with the ingredients and proportions shown in Table 4, and was tested both with and without deoxidizer (oxygen scavenger) present in the storage container along with the formulated pharmaceutical composition. Formula 5 is formulated material made with the ingredients and proportions shown in Table 5. Materials were stored at 60° C. or 40° C. for up to 6 months, as indicated in Table 1 above to test stability. Both formulations (Formula 4 and Formula 5) were prepared using the same batch of Compound A-TA. The lowest amounts of Impurity B, which is an oxidized derivative of Compound A, were found when the formulated pharmaceutical compositions was stored in a container in the presence of an oxygen scavenger (Deoxidizer CD20). Thus packaging the pharmaceutical compositions comprising Compound A-TA in the presence of an oxygen scavenger reduces formation of at least one impurity during prolonged storage.

Accordingly, in some embodiments, the pharmaceutical composition comprising Compound A-TA is stored under conditions that reduce exposure to oxygen, humidity, or both. In some embodiments, the pharmaceutical composition is stored in the presence of a protective agent, or packaged together with a protective agent, or it can be stored in an inert atmosphere, or it can be film coated. Suitable protective agents for this purpose include the following desiccants and deoxidizers:

Desiccants, including but not limited to typical desiccants such as:
1) silica gel desiccant, e.g., activated silica gel;
2) molecular sieve desiccant—a synthetic zeolite with strong absorbability to water molecules. The pore size of molecular sieve materials can be controlled by different processing techniques, so in addition to adsorbing water vapor, they can also adsorb other gases.
3) fiber desiccants.

Deoxidizers, including oxygen absorbent products known in the art, for example, deoxidant canisters containing iron, and commercial oxygen-absorbing PharmaKeep® canisters made by Mitsubishi Gas Chemicals Company, including CD20, CD10, KD10, and KD20, which are designed for use with pharmaceutical products.

Certain of the oxygen absorbers can be used in combination with the desiccants, such as molecular sieves and/or activated silica gel, as is known in the art.

Other methods to reduce oxidation of Compound A-TA in the pharmaceutical compositions of the disclosure include adding one or more antioxidants to the formulated pharmaceutical composition, e.g. sodium bisulfite, sodium sulfite, sodium thiosulfate, sodium pyrosulfite, butyl hydroxy anisole (BHA), antioxidant –264 (BHT), vitamin E and the like; or maintaining the pharmaceutical composition in an atmosphere of inert gas that is substantially free of oxygen and/or humidity, e.g. dry nitrogen or argon.

A separately packaged oxygen absorber can effectively reduce the amount or oxygen in the package and protect the product from being oxidized during prolonged storage. Many suitable oxygen absorbent products are known in the art; for example, deoxidant canisters containing iron can be used. Other examples include oxygen-absorbing PharmaKeep® canisters made by Mitsubishi Gas Chemicals Company, including CD20, CD10, KD10, and KD20, which are designed for use with pharmaceutical products. The oxygen absorbers can be used in combination with desiccants, such as molecular sieves and/or activated silica gel. Table 2 shows the improvement in impurity profile achieved by including PharmaKeep® CD20 oxygen absorber in a container with a pharmaceutical composition comprising Compound A-TA in a test of stability at elevated temperature (40° C.).

When encapsulated as described herein, and stored in an opaque HDPE bottle with conventional LDPE cap in the presence of an effective deoxidizer (e.g., PharmaKeep® CD20), Compound A-TA is highly stable when stored at 40° C. and 75% relative humidity for up to 6 months, or at 25° C. and 60% relative humidity for up to 24 months.

Accordingly, in some embodiments, the capsule or tablet comprising Compound A-TA is packaged inside an opaque High-Density Polyethylene (HDPE) bottle and capped with an opaque High-Density Polyethylene (HDPE) or low-density polyethylene (LDPE) cap. Optionally, the bottle also contains a protective agent, e.g., silica gel or activated carbon or activated zeolite (molecular sieve) desiccant, and optionally the bottle also contains a deoxidizer, such as a deoxidizing canister product like PharmaKeep® CD10, CD20, KD10 or KD20. In some embodiments the protective agent(s) is/are contained in a canister, sachet, envelope or similar receptacle inside the bottle to prevent the protective agent from directly contacting the pharmaceutical composition, while permitting the protective agent to be exposed to any oxygen inside the bottle.

In some embodiments, the bottle containing capsules or tablets comprising Compound A-TA contain an oxygen trapping agent, such as iron powder, catechol, calcium, ascorbic acid, or calcium oxide in a container such as a ventilated plastic canister, using methods and products known in the art for protection of pharmaceuticals. In some embodiments, the oxygen trapping agent is a PharmaKeep® product or StabilOx product, which can be a pouch or a canister containing a proprietary oxygen trapping material, and optionally also containing a desiccant. Thus in some embodiments, the invention provides a packaged pharmaceutical product, which comprises a pharmaceutical composition comprising Compound A-TA and a protective agent, which can be a desiccant, antioxidant, oxygen removal agent, or opaque coating, or an inert gas used to displace air in the bottle or other container used to package the pharmaceutical products. In some embodiments, the pharmaceutical composition, which may be in the form of dosage units of Compound A-TA such as capsules or tablets, is packaged in a bottle, and the protective agent is separately packed in the same bottle, which is preferably substantially air tight. In some of these embodiments, a deoxidizing agent inside a canister is added to the bottle along with the pharmaceutical composition. Optionally, the deoxiding agent is selected from CD and KD products, e.g CD10 and KD10 and CD20 and KD20, products in the PharmaKeep® product line by Mitsubishi, that are designed for use with pharmaceuticals, and which provide protection for the composition.

In some embodiments, the pharmaceutical composition comprising Compound A-TA, optionally in the form of dosage unit(s) of Compound A-TA, is packaged in a sealed bag, box, drum, or other container and is protected by an atmosphere of an inert gas, e.g. dry nitrogen or argon.

The present methods can be used for any suitable purpose. In some embodiments, the present methods can be used to treat and/or prevent a proliferation disorder, a cancer, a tumor, an inflammatory disease, an autoimmune disease, psoriasis, dry eye or an immunologically related disease or lupus in the subject. The present methods can be used to treat and/or prevent any suitable proliferation disorder. Exemplary proliferation disorders include sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer. Of specific interest are methods of using the solid forms of Compound A-TA, pharmaceutical compositions, and dosage units containing these solid forms, for treatment of a condition selected from lupus, rheumatoid arthritis, chronic myeloid leukemia, and chronic lymphocytic leukemia.

EXAMPLES

Exemplary chemical entities, pharmaceutical compositions, and methods of making such compounds and compositions will now be described by reference to the specific examples that follow. Artisans will recognize that, for the chemical syntheses, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the examples below may be performed in any order that is compatible with the functionality of the particular pendant groups. Each of the reactions depicted in the general schemes is preferably run at a temperature from about 0° C. to the reflux temperature of the organic solvent used. Some of the reactions described in the examples provided below are run at a temperature from about −10° C. to about 100° C. With respect to the pharmaceutical composition examples, one of ordinary skill in the art will recognize that variations of the examples that follow may be appropriate.

The examples described herein are provided solely to illustrate representative embodiments of the invention. Accordingly, it should be understood, that the invention is not to be limited to the specific conditions or details described in these or any other example discussed herein, and that such examples are not to be construed as limiting the scope of the invention in any way. Throughout the specification, any and all references are specifically incorporated herein by reference in their entireties.

The following abbreviations may be used in the specification and examples: DCM=dichloromethane; DIEA=DIPEA=N,N-diisopropylethylamine; DMF=N,N-dimethylformamide; EtOH=ethanol; EtOAc=ethyl acetate; MeOH=methanol; t-BuOH=tert-butyl alcohol; and THF=tetrahydrofuran. Abbreviations used herein have their commonly understood meaning in the art unless otherwise indicated.

Compound A was synthesized by three different methods. Strategy/Route 1:

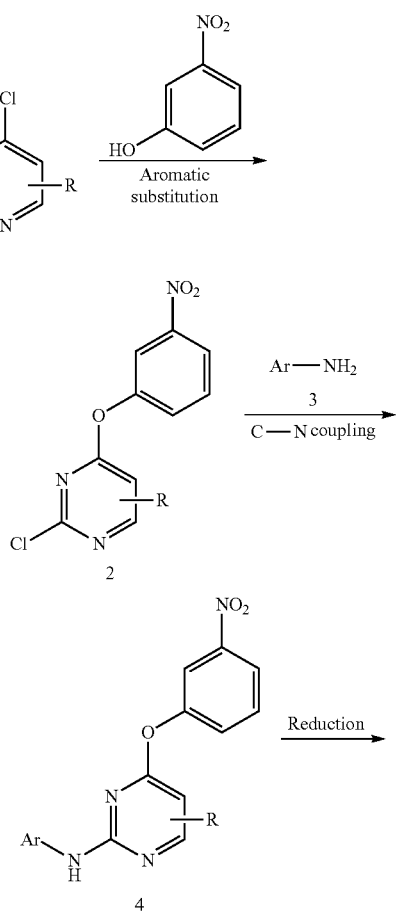

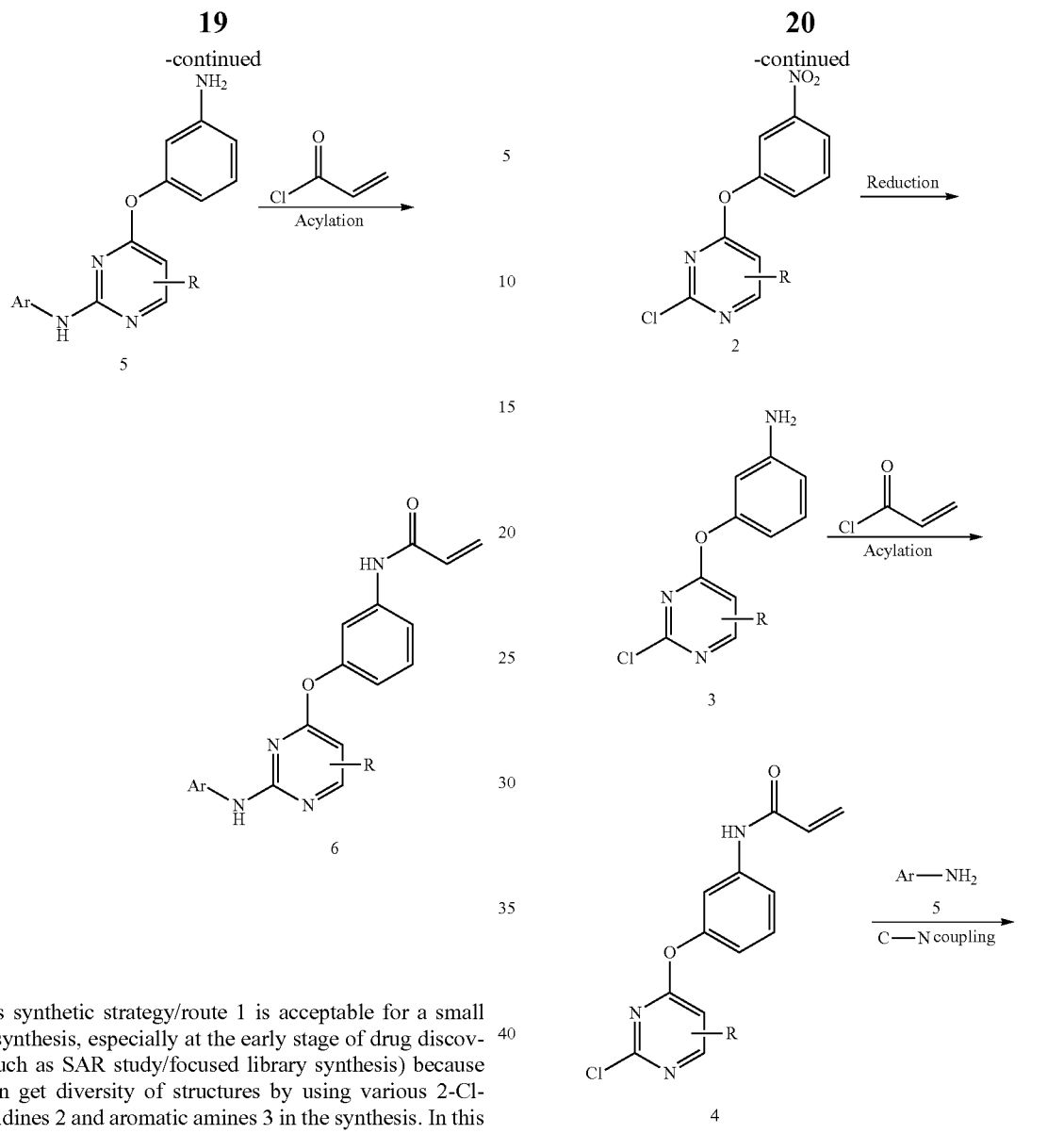

This synthetic strategy/route 1 is acceptable for a small scale synthesis, especially at the early stage of drug discovery (such as SAR study/focused library synthesis) because we can get diversity of structures by using various 2-Cl-pyrimidines 2 and aromatic amines 3 in the synthesis. In this strategy, the key intermediates 2 and 3 are coupled by Pd-catalyzed C—N coupling reaction, followed by a reduction and an acylation to obtain the targeted compound 6. The drawback of this synthesis is that the acylation reaction at the final step is often influenced by other NH groups in the molecule, which will result in an un-desired side-product (impurity). To overcome this disadvantage, we decided to modify this synthetic strategy/route by running the acylation before the coupling reaction (see strategy/route 2).

Strategy/Route 2:

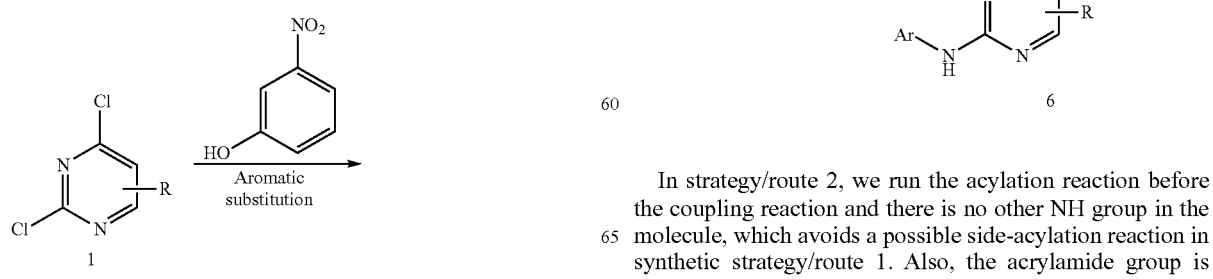

In strategy/route 2, we run the acylation reaction before the coupling reaction and there is no other NH group in the molecule, which avoids a possible side-acylation reaction in synthetic strategy/route 1. Also, the acrylamide group is found to be very stable during the final coupling reaction.

Strategy/Route 3.

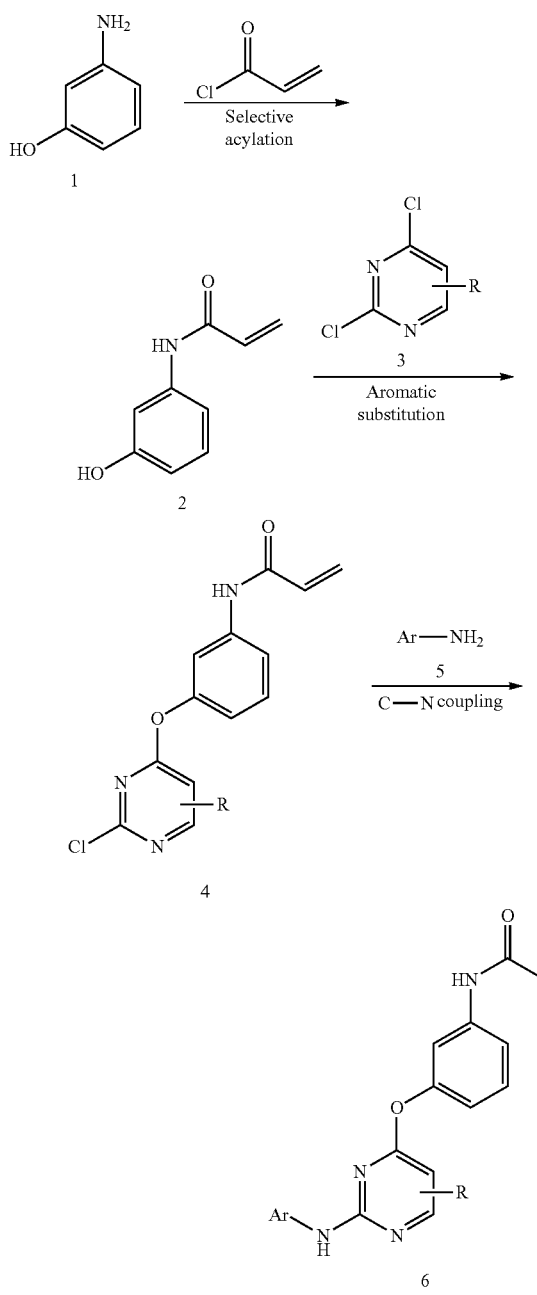

In strategy/route 3, the efficiency of the synthesis is further improved by shortening the synthesis of 2-Cl-pyrimidines 4 by employing inexpensive starting material 3-aminophenol instead of 3-nitrophenol (a reduction reaction is eliminated). The acylation reaction between 3-aminophenol and acryloyl chloride is found to be very selective.

Furthermore, during the process development, different purities of the starting material, 2-Cl-pyrimidine 4, was explored, and the results showed that different batches of 2-Cl-pyrimidine 4 with a purity range of 97.8-99.2% all gave product 9 (Compound A) that met the acceptance criteria.

Based on results from testing of the three synthetic strategies, route 3 was used for preparation of batches of Compound A for the compositions and experiments described herein. as the final synthetic strategy/route for the synthesis of Compound A freebase.

This synthetic route begins with commercially available (S)-tert-butyl 3-aminopyrrolidine-1-carboxylate 1, whose ee % (enantiomeric purity) is at least 98.5%. All the reactions are performed under mild conditions with moderate to excellent yields. Most importantly, the whole process leads to retention of stereochemistry at the final product Compound A freebase. Thus, this synthetic route is selected for further development and for scale-up manufacturing.

After finalizing the synthetic route, optimization of the reaction conditions for each step of the synthesis was initiated, and the manufacturing scale was gradually scaled up to over 5 kg.

Example 1. Synthesis of Starting Material (8)

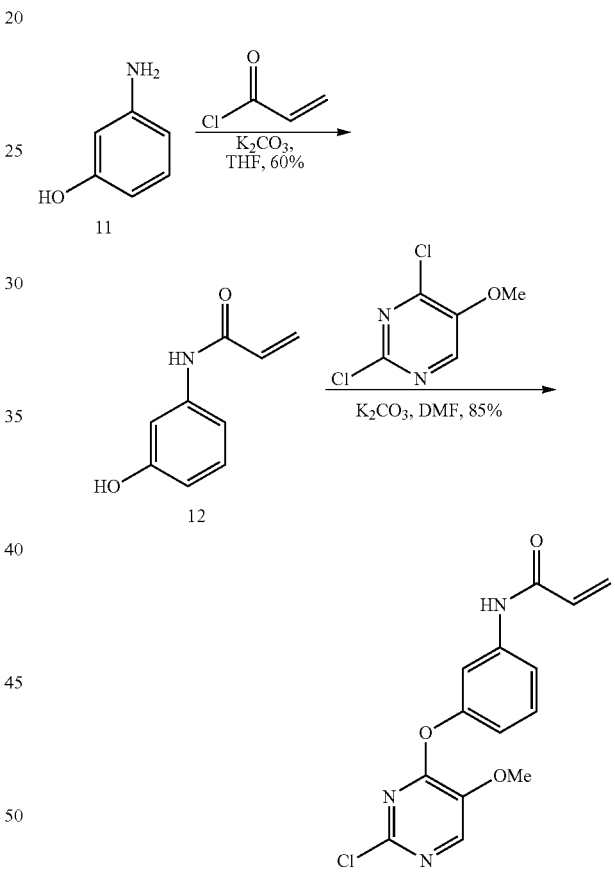

Step 1: Synthesis of N-(3-hydroxyphenyl)acrylamide (12)

A 30 L jacketed reactor was equipped with a cooling system which was set to −20° C. 3-aminophenol 11 (2.3 kg, 21.1 mol), THF (15 L) and $K_2CO_3$ (4.5 kg, 32.6 mol) were added to this reactor with mechanical stirring. When the temperature inside the reactor reached ~−10° C., acryloyl chloride (2 kg, 22.1 mol) was added drop-wise into the reactor. The internal temperature was kept below 0° C. during the addition. The reaction was stirred for 1 h after the addition of acryloyl chloride. At this point, an in-process TLC analysis (ethyl acetate/petroleum ether/HOAc=2/1/0.1 as mobile phase) is performed to confirm the completion of the reaction. Water (10 L) was then added slowly to quench the reaction. The mixture was concentrated down to remove THF under reduced pressure. Ethyl acetate (10 L) was added and the batch was agitated for 30 min. The aqueous layer was separated and extracted with ethyl acetate (10 L×4) until the absence of compound 12 in the aqueous layer (by TLC). The organic layers were combined and washed with water (3 L×3)

The extraction-washing process was repeated two more times to maximize the recovery of compound 12 from the water layer above. All the ethyl acetate layers were combined, dried over Na2SO4 and filtered. The filtrate was concentrated down under reduced pressure to a volume of ~5 L. The concentrated solution stood overnight at room temperature and the precipitate was collected to afford crude compound 12, which was further purified by mixing it with cold ethyl acetate (4 L) under vigorous stirring for 30 min. The solid product was collected and dried under vacuum to afford compound 12 (2.1 kg, 60% yield) as a white solid.

Step 2: Synthesis of N-(3-((2-chloro-5-methoxypyrimidin-4-yl)oxy)phenyl)acrylamide (8)

DMF (15 L) was charged to the reactor equipped with a heater which was set to 75° C. Compound 12 (3.05 kg, 18.7 mol), 2, 4-dichloro-5-methoxypyrimidine (3.3 kg, 18.4 mol) and K2CO3 (3.85 kg, 27.9 mol) were then added with mechanical stirring. When the internal temperature reached 70° C., the mixture was agitated for another 4~4.5 h. At this point, an in-process TLC analysis (ethyl acetate/petroleum ether/Et3N=2/2/0.1 as mobile phase) indicated that the reaction was complete. The mixture was then cooled down to room temperature, filtered, and washed with DMF (1 L). The resulting DMF solution (filtrate) was slowly poured into water (10 times of the volume of DMF). The precipitate was collected and washed with water (~4 L) until the water layer was neutral, and then dried to give the crude 8.

The crude was further purified by mixing it with ethyl acetate (~45 L, 8 times of the weight of the crude compound 8). The resulting suspension was heated to reflux and stirred for 1 h. After cooling down, the solid was collected, washed with ethyl acetate (1 L×2), and dried to afford compound 8 (4.79 kg, 85% yield) as a white solid.

Example 2. Synthesis of Compound A

Step 1: Synthesis of (S)-tert-butyl 3-((4-nitrophenyl)amino)pyrrolidine-1-carboxylate (3)

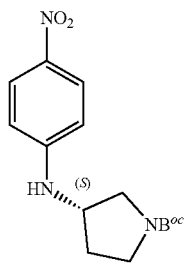

(S)-tert-butyl 3-aminopyrrolidine-1-carboxylate 1 (5.996 kg, 32.19 mol), 1-fluoro-4-nitrobenzene 2 (4.622 kg, 32.75 mol), DMSO (19.8 L) and Et3N (4.840 kg, 47.83 mol) were charged to a 50 L-reactor equipped with a condenser. The reaction mixture was then heated with a water-bath (90~95° C.) and stirred for 12 hours (inside temperature was kept between 85~95° C. during this period of the time). At this point, an in-process TLC analysis (ethyl acetate/petroleum ether=1/2 as mobile phase) indicated that the reaction was complete. The reaction mixture was then cooled to room temperature. The resulting solution was slowly transferred to a reactor which contained ice-water (60 L), and a dense precipitation was formed. The resulting slurry was stirred vigorously for 2 hours. The yellow precipitate was then filtered, washed with water (12 L×2), and dried at 40~45° C. to give compound 3 (9.6 kg, 97.09% purity by HPLC, 96.96% yield) as a yellow solid, which was used for next step reaction without further purification.

Step 2: (S)-tert-butyl 3-(methyl(4-nitrophenyl)amino)pyrrolidine-1-carboxylate (4)

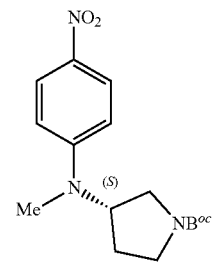

A 100 L-reactor was charged with compound 3 (9.6 kg, 31.23 mol) and DMF (48 L) and stirred. After compound 3 was completely dissolved, the resulting yellow solution was cooled to 0~5° C., and NaH (60%, 1.876 kg, 46.90 mol) was added slowly (portion by portion, keeping the temperature inside the reactor between 0~5° C.). The reaction mixture was stirred for 15 min and then CH3I (5.326 kg, 37.52 mol) was slowly added, maintaining the internal temperature between 0~5° C. Once the addition was completed, the cooling was removed, and the mixture was stirred for 1 hour. At this point, an in-process TLC analysis (ethyl acetate/petroleum ether=1/6 as mobile phase) indicated that the reaction was complete. Cold water (12 L) was then added to quench the reaction, and the reaction mixture was stirred for another hour.

Extraction with ethyl acetate: The reaction mixture was roughly divided into three equal portions. To one portion of the reaction mixture in a 100 L-reactor, water (42 L) was added. The resulting solution was extracted with ethyl acetate (24 L). The aqueous layer was removed. The organic layer was washed with water (18 L×2) and then filtered through a Celite® layer. The same procedure was repeated for the other two portions of the reaction mixture. The combined filtrates (organic layers) were concentrated under reduced pressure. The resulting solid was further dried to give compound 4 (10.080 kg, 97.17% purity by HPLC, 100.12% yield) as a brown solid, which was used for next step reaction without further purification.

Step 3: Synthesis of (S)—N-methyl-N-(4-nitrophenyl)pyrrolidin-3-amine hydrochloride (5)

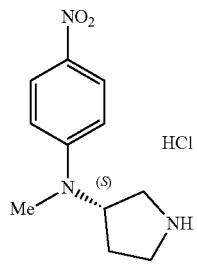

A 100 L-reactor was charged with compound 4 (10.045 kg, 31.26 mol), methanol (10 L) and dichloromethane (10 L). The reaction mixture was stirred at a speed of 120~150 rpm until compound 4 was completely dissolved. The resulting yellow solution was cooled to 0~5° C., HCl/MeOH (8 M, 20 L) was slowly added with stirring. Once the addition was complete, the reaction mixture was stirred for another 0.5 h at this temperature. The cooling system was removed and the reaction mixture was allowed to warm up to room temperature, and continued stirring for another 16.5 h (precipitation formed). At this point, an in-process TLC analysis (ethyl acetate/petroleum ether=1/1 as mobile phase) indicated that the reaction was complete. The suspension was then re-cooled to 0~5° C. The resulting precipitate was collected, washed with ethyl acetate (3 L×2), and dried at 40~45° C. to give compound 5 (7.060 kg, 99.93% purity by HPLC, 88.05% yield) as a yellow solid, which was used for next step reaction without further purification.

Step 4: Synthesis of (S)-1-(3-(methyl(4-nitrophenyl)amino)pyrrolidin-1-yl)ethenone (6)

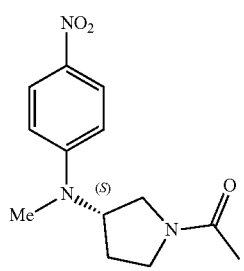

Et₃N (6.940 kg, 68.65 mol) was added to a solution of compound 5 (7.052 kg, 27.58 mol) in methanol (41 L) and dichloromethane (32 L). The resulting yellow solution was cooled to 0~5° C., acetyl chloride (2.590 kg, 32.99 mol) was then added drop-wise with stirring while keeping the reaction temperature below 5° C. Once the addition was complete, the reaction mixture was stirred for another 0.5 h at this temperature. At this point, an in-process TLC analysis (ethyl acetate as mobile phase) indicated that the reaction was complete. The reaction mixture was concentrated under reduced pressure. The residue was re-dissolved in ethyl acetate (72 L), and washed with water (36 L×1, 18 L×2). The organic phase was concentrated under reduced pressure. This crude was suspended in heptane/ethyl acetate (v/v=1:1, 24 L) with vigorously stirring for 1 h. The resulting suspension was filtered. The solid was collected, washed with heptane (6 L), and dried to give compound 6 (6.430 kg, 99.84% purity by HPLC, 89.25% yield) as a yellow powder, which was used for next step reaction without further purification.

Step 5: Synthesis of (S)-1-(3-((4-aminophenyl)(methyl)amino)pyrrolidin-1-yl)ethanone (7)

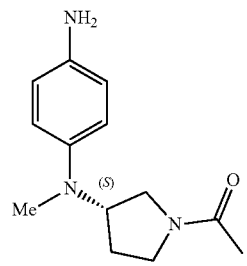

Pd/C (10% on activated carbon, 257.00 g, 0.241 mol), THE (51.3 L), methanol (12.8 L) and compound 6 (6.420 kg, 24.39 mol) were charged into a 100 L-reactor. The air in the reactor was removed by nitrogen flow. Hydrogen pressure was applied at normal atmosphere by bubbling. The hydrogen flow was controlled to maintain the internal temperature between 25~35° C. The reaction mixture was stirred for 48 h. At this point, an in-process TLC analysis (dichloromethane/methanol=15:1 as mobile phase) indicated that the reaction was complete. The reaction mixture was filtered through Celite® to remove catalyst. The filtrate was concentrated under reduced pressure to give compound 7 (5.498 kg, 98.00% purity by HPLC, 96.6% yield) as a black oil, which was used for next step reaction without further purification.

Step 6: Synthesis of (S)—N-(3-((2-((4-((1-acetylpyrrolidin-3-yl)(methyl)amino)phenyl)amino)-5-methoxypyrimidin-4-yl)oxy)phenyl)acrylamide (9: Compound A)

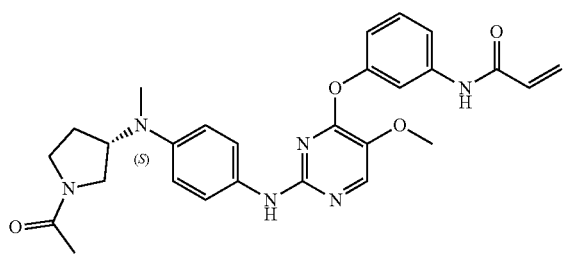

t-BuOH (16 L) was added to a jacketed 30 L-reactor with mechanical stirring at a speed of 110 rpm. Compound 7 (975.0 g, 4.18 mol) and compound 8[1] (1277.5 g, 4.18 mol, synthesized separately) were added. The reaction mixture was stirred for 5-10 min. Potassium carbonate (805.6 g, 5.82 mol), tris(dibenzylideneacetone) dipalladium (76.5 g, 0.084 mol) and dicyclohexyl (2',4',6'-triisopropylbiphenyl-2-yl) phosphine (74 g, 0.155 mol) were then added with stirring. The air in the reactor was removed by nitrogen flow. Hot water (95~97° C.) was applied through the jacket to heat the reactor. The reaction mixture was stirred for 7 h, during this period of the time the reaction temperature was kept between 82-85° C. At this point, an in-process HPLC analysis indicated less than 5% compound 7 unreacted. The mixture was then allowed to cool to 50° C., filtered through mixture of silica gel (~300 mesh, 2 kg) and Celite® (2 kg), and washed with ethyl acetate (8 L). The combined filtrate was concentrated under reduced pressure to afford crude 9.

The crude was re-dissolved in ethyl acetate (20 L), and transferred to a 50 L-reactor. The resulting solution was washed with brine (12 L×3). The lower layer was removed. The organic layer was dried over anhydrous $Na_2SO_4$ (2 kg), filtered and concentrated down under reduced pressure to a residual volume of ~5 L. The resulting solution was allowed to cool down to room temperature, and left it standing overnight with stirring. Precipitation was formed as an off-white solid. The precipitate was collected and dried with vacuum to afford a $2^{nd}$ crude (1300 g, 96.4% purity by HPLC, 61.9% yield), which was sealed to avoid light, and stored in a dry place at room temperature for next step of removal of heavy metal Palladium.

Three (3) syntheses of the $2^{nd}$ crude of compound 9 were combined for further processing to remove the Palladium heavy metal.

Palladium Removal Process with TMT (s-triazine-2,4,6-trithiol: 1,3,5-triazine-2,4,6-trithiol)

The $2^{nd}$ crude product (2950 g, 5.88 mol) was charged into 100 L-reactor containing THF (29.5 L) and dichloromethane (29.5 L), followed by agitation at room temperature until the compound 9 was completely dissolved. Then TMT (100 g, 0.85 mol), activated carbon (295 g) and silica gel (300~400 mesh, 295 g) were added. The resulting suspension was stirred at room temperature for 48 h, and then filtered through Celite® and washed with EtOH (5.4 L). The combined filtrates were concentrated under reduced pressure. The resulting residue was re-dissolved in dichloromethane (29.5 L). This solution was washed with diluted aqueous ammonia (1.5-2.0%, 5.4 L) and water (13 L×2). The organic layer was separated, dried over $Na_2SO_4$ (1.34 kg), filtered and concentrated under reduced pressure to remove most of dichloromethane (no precipitation, ~4.5 L remaining). Ethyl acetate (27 L) was added slowly. The precipitates (similar as re-crystallization) were collected and dried under vacuum to afford the final desired product 9 (2398 g, 98.91% purity by HPLC, 81.3% yield from the $2^{nd}$ crude of compound 9) as an off-white solid.

Example 3. Synthesis of Compound A-TA as Crystalline Dihydrate

Synthesis of(S)—N-(3-((2-((4-((1-acetylpyrrolidin-3-yl)(methyl)amino)phenyl) amino)-5-methoxypyrimidin-4-yl)oxy)phenyl)acrylamide L-(+)-tartrate dihydrate (10, Compound A-TA)

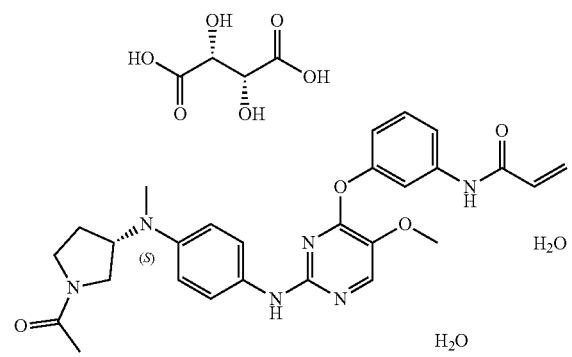

Three (3) batches of compound 9 (Compound A) were combined for this process step.

Compound 9 (5918 g, ~98.7% purity) was dissolved in dichloromethane (60 L) at 25° C. This solution was concentrated under reduced pressure at 40° C. to remove about 55 L dichloromethane. Ethyl acetate (30 L) was added slowly with stirring. The mixture was cooled to ~20° C. for crystallization. The resulting crystals were collected, washed with cold ethyl acetate (10 L), and dried under vacuum at 45° C. overnight to afford compound 9 (4950 g) in 99.19% purity by HPLC, as an off-white powder, which was used for the salt formation step.

A 100 L-reactor was charged with acetone (30 L) and water (3.5 L). The purified sample of Compound 9 (freebase, 4.7 kg, 9.36 mol) was added with stirring followed by rinsing with acetone (12.3 L). The resulting suspension was stirred vigorously at 45° C. until compound 9 was completely dissolved (~1.5 h). A solution of L-(+)-tartaric acid (1.471 kg, 9.8 mol) in water (1.2 L) was then added slowly with stirring. The solution was allowed to cool to room temperature and continued stirring for 5 h. The resulting precipitates were collected, washed with acetone (1 L), and dried at 45° C. for 24 h. The solid was then ground and sieved to a 60-mesh size and air-dried at room temperature to afford the desired product 10 (Compound A-TA) as an orange powder (5.8 kg, 99.3% HPLC purity, 90.0% yield).

Infrared Spectrum (IR)

The hydroxyl stretch gives absorption peak in the 3420 $cm^{-1}$ region. The amine stretch gives absorption peak in the 3302 $cm^{-1}$ region. The alkyl stretch gives absorption peaks in 2822, 2892, 2953, 3047 and 3117 $cm^{-1}$ regions. The ammonium ($NH^+$) stretch gives absorption peaks in 2310 and 2345 cm$^{-1}$ regions. The bending of ammonium (NH$^+$) group gives absorption peak in 1956 cm$^{-1}$ region. The carbonyl group stretch in the carboxylic acid moiety gives absorption peaks in 1723 and 1610 cm$^{-1}$ regions. The carbonyl group stretch in the amide moiety gives absorption peak in 1660 cm$^{-1}$ region. The amine group bending in the amide moiety gives absorption peak in 1520 cm$^{-1}$ region. The C—N bond stretch in the amide moiety gives absorption peak in 1266 cm$^{-1}$ region. Then benzene skeletal vibration gives absorption peaks in 1433, 1461, and 1539 cm$^{-1}$ regions. The alkyl aryl ether stretch gives absorption peaks in the 1227 cm$^{-1}$ region. The biaryl ether stretch gives absorption peaks in the 1203 cm$^{-1}$ region.

Ultraviolet Spectroscopy

See

Table for the UV absorption data and analysis.
(1) Sample preparation: Sample was prepared in a solution at a specified concentration, and placed in a 1.00-cm cell.
(2) Wavelengths: 200~ 400 nm.
(3) Solvents: methanol, 0.1 M HCl aqueous, 0.1 M NaOH aqueous.
(4) Concentration: 3.3×10$^{-5}$ M.

UV Spectrum: Samples in methanol, 0.1 M HCl aqueous and 0.1 M NaOH aqueous solution were measured. The measurement range was from 200-400 nm.

TABLE 2

UV Absorption Data and Analysis.

| | Sample | | | |
|---|---|---|---|---|
| | λmax (nm) | A | ε (L · mol$^{-1}$ · cm$^{-1}$) | |
| Methanol | 204.6 | 1.5417 | 4.62 × 10$^4$ | n-σ* transition |
| | 280.2 | 1.1929 | 3.58 × 10$^4$ | π-π* transition |
| 0.1 mol/L HCl | 268.6 | 1.0002 | 3.00 × 10$^4$ | π-π* transition |
| 0.1 mol/L NaOH | 277.0 | 1.0683 | 3.20 × 10$^4$ | π-π* transition |

Figure 4:
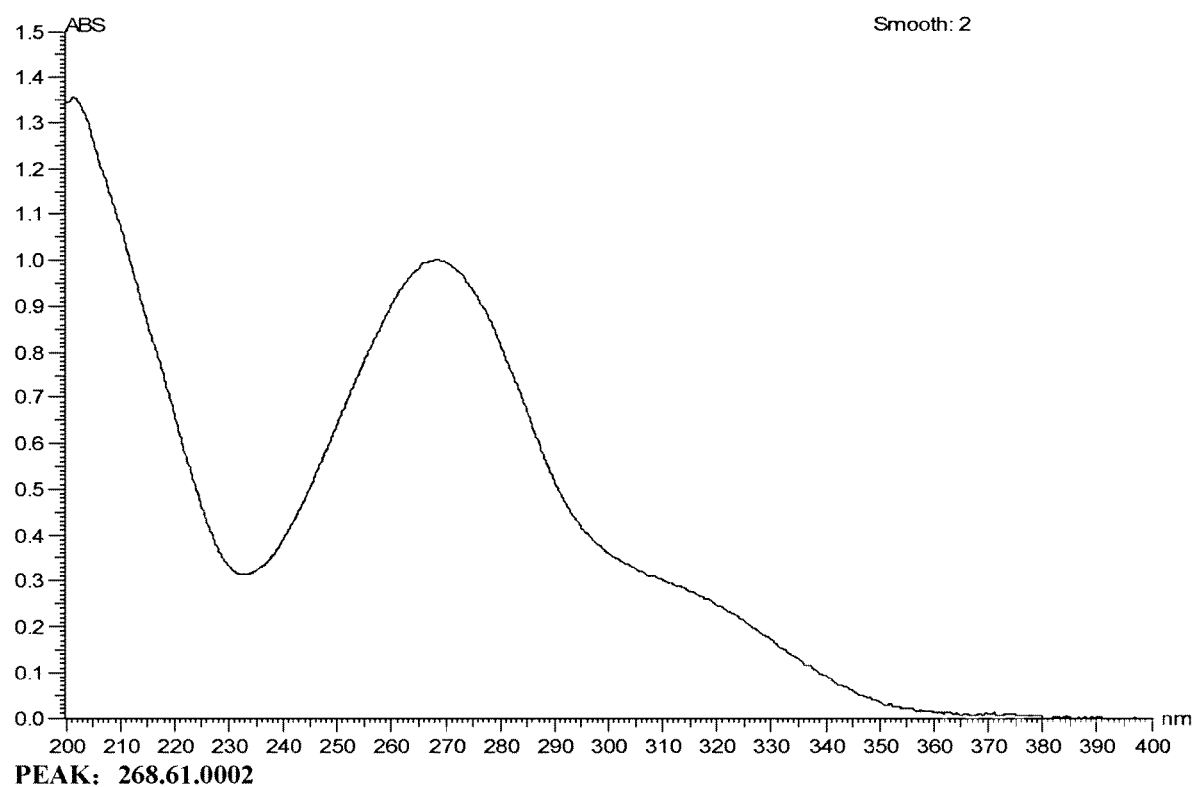
FIG. 4 shows an Ultraviolet spectrum of Compound A-TA in acidic medium.
Figure 5:
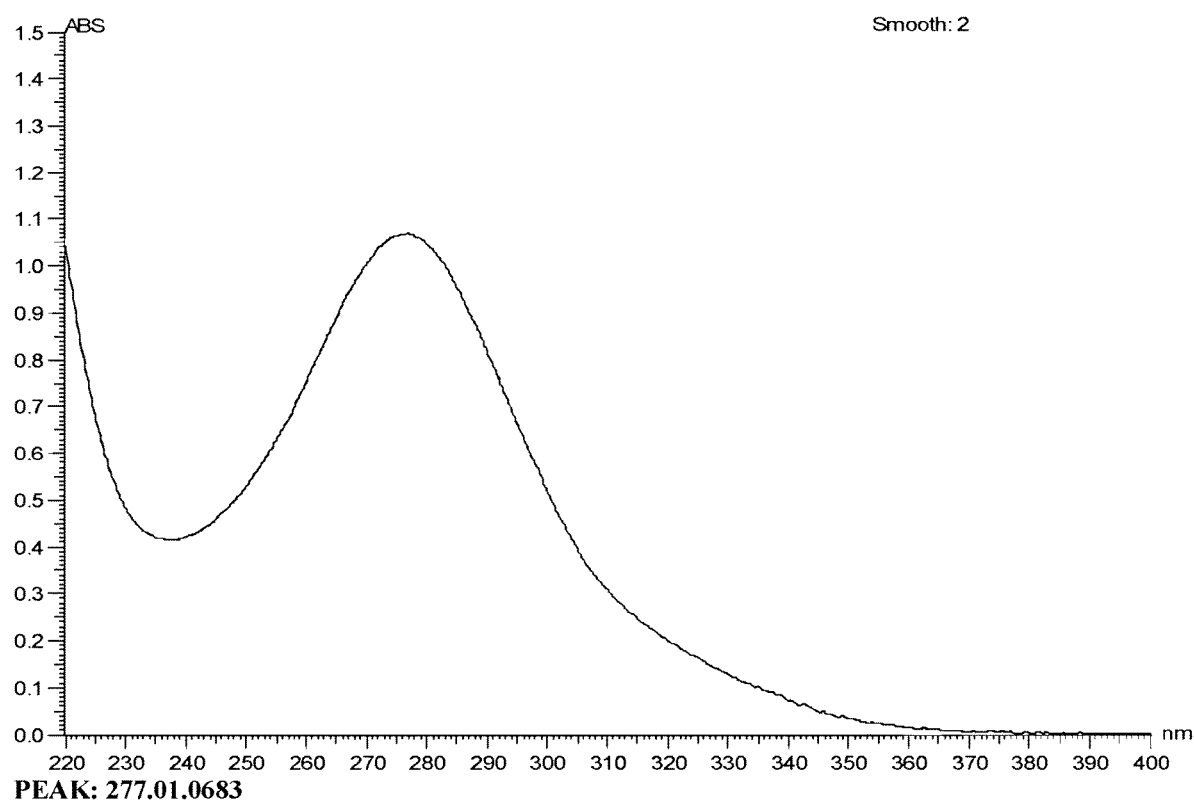
FIG. 5 is an Ultraviolet spectrum of Compound A-TA in basic aqueous medium

The UV spectra (F, FIG. 4 and FIG. 5) are shown below.

The two maximum absorptions (λ$_{max}$) of the sample in neutral solvent (methanol) are respectively at 204.6 nm (ε=4.62×10$^4$) and 280.2 nm (ε=3.58×10$^4$). The absorption at 204.6 nm is identified as n-σ* transition of hetero atom, while the absorption at 280.2 nm is identified as sample's K absorption band caused by π-π* transition of conjugated double bonds in benzene ring. In an acidic solvent, the K absorption band of conjugated systems has their λ$_{max}$ at 268.6 nm (ε=3.00×10$^4$). In a basic solvent, the K absorption band of conjugated systems has their λ$_{max}$ at 277.0 nm (ε=3.20×10$^4$).

NMR

Figure 6:
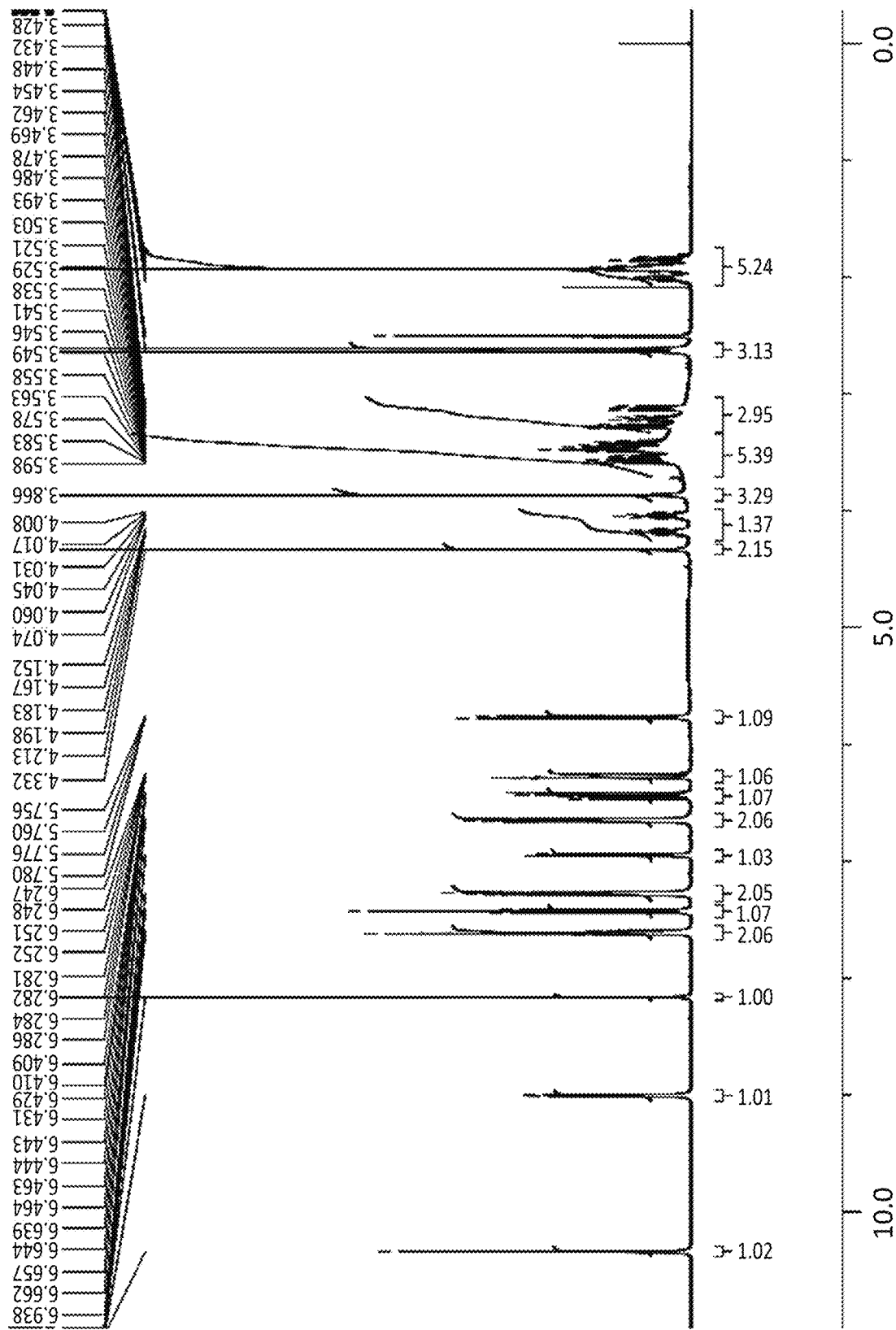
FIG. 6 is a proton nuclear magnetic resonance ($^1$H NMR) spectrum of Compound A-TA in $d^6$-DMSO.

Solvent: DMSO-d6; Internal standard: trimethylsilylpropionate (TSP) The $^1$H-NMR spectrum is shown in FIG. 6.

X-Ray Powder Diffraction

Test condition: power 40 kV×250 mA, Cu Kα radiation

Scanning mode: straight scanning, step width: 0.02°, scanning area (2θ): 3°-40°, scanning rate: 5°/min.

The X-ray powder diffraction pattern is shown in F.

Thermo-Gravimetric Analysis

Sweeping gas: N$_2$ 120 mL/min, programming rate: 10° C./min

Range of temperature: from room temperature to 280° C.

TGA trace is shown in FIG. 7.

Differential Thermal Analysis

Sweeping gas: N$_2$ 50 mL/min, programming rate: 10° C./min

Range of temperature: from room temperature to 200° C.

Figure 8:
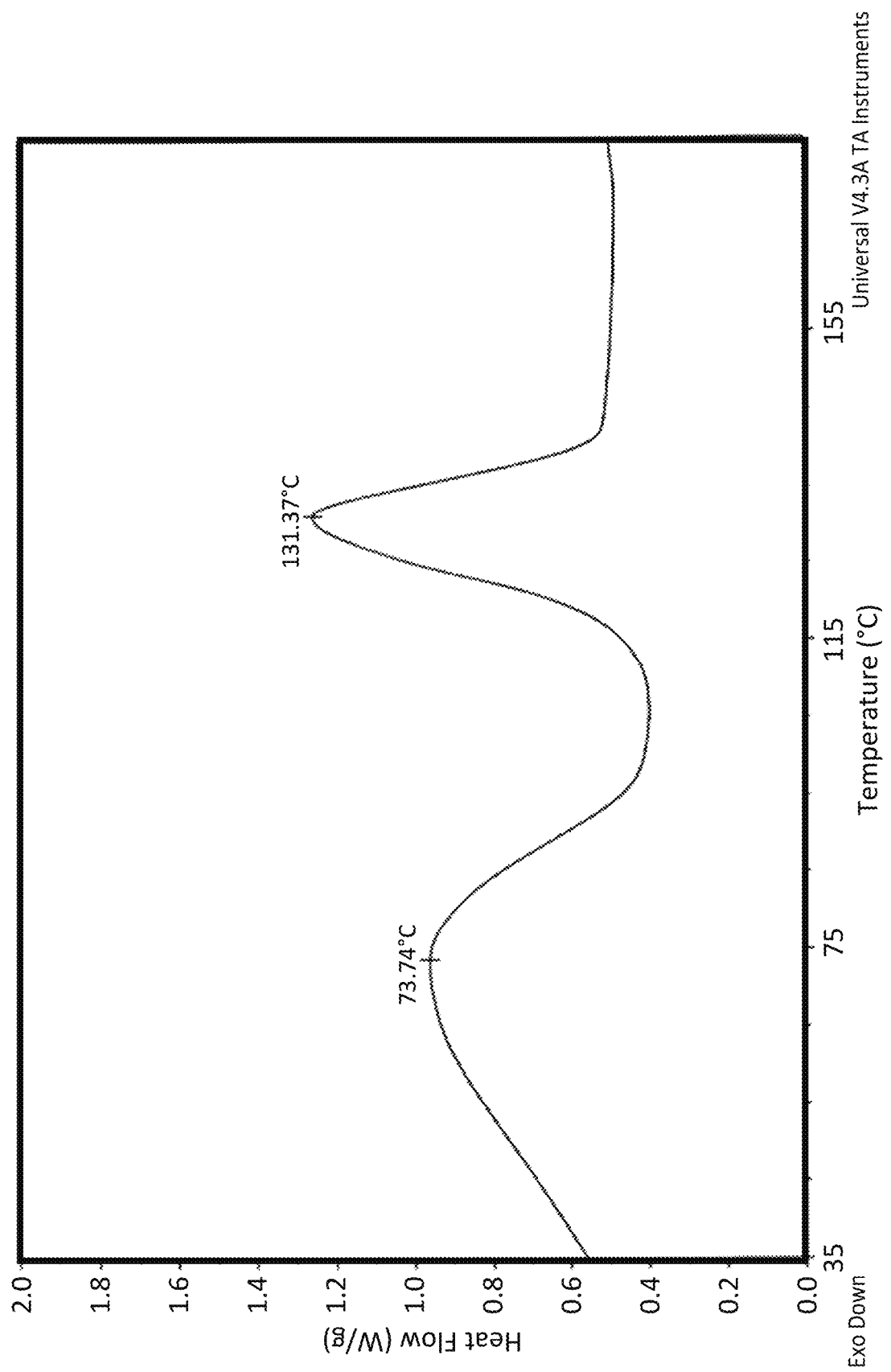
FIG. 8 shows the differential scanning calorimetry curve of polymorph Form I of Compound A-TA.

The DSC trace is shown in FIG. 8.

Various conditions were tested to try to produce crystalline forms and identify useful polymorphic forms of Compound A-TA. Table briefly summarizes the conditions used for polymorph preparation and the results obtained.

TABLE 3

A Summary of Polymorph Formation Conditions for Compound A-TA.

| Solvents/Method | Synthesis/Crystallization | Polymorph Form |
|---|---|---|
| 1. EtOH:H$_2$O = 1:1 | Freebase (1.0113 g, 2.0 mmol) was dissolved in EtOH (5 mL) and H$_2$O (5 mL) at 70° C. with stirring. Then L-(+) tartaric acid (0.3174 g, 2.1 mmol) was added. The solution was cooled down to RT with stirring. Crystals appeared in 30 min. The resulting crystals were collected and dried to yield the product (1.2332 g, 88.5%). | Form 1 - Elemental Analysis: C 53.21; N 11.84; H 5.74 |
| 2. EtOH:H$_2$O = 4:6 | Freebase (1.0054 g, 2.0 mmol) was dissolved in EtOH (6.5 mL) and H$_2$O (10.5 mL) at 70° C. with stirring. Then L-(+) tartaric acid (0.3152 g, 2.1 mmol) was added. The solution was cooled down to RT with stirring. Crystals appeared in 60 min. The resulting crystals were collected and dried to yield the product (1.1887 g, 85.3%). | Form 1 - Elemental Analysis: C 53.36; N 11.97; H 5.73 |
| 3. EtOH:H$_2$O = 9:1 | Freebase (1.0008 g, 2.0 mmol) was dissolved in EtOH (9 mL) and H$_2$O (1 mL) at 70° C. with stirring. Then L-(+) tartaric acid (0.3142 g, 2.1 mmol) was added. The solution was cooled down to RT with stirring. Crystals appeared in 30 min. The resulting crystals were collected and dried to yield the product (1.2325 g, 88.4%). | Form 1 - Elemental Analysis: C 53.27; N 11.96; H 5.65 |
| 4. propanol:H$_2$O = 7:3 | Compound A-TA (0.5 g) was dissolved in propanol (7 mL) and H$_2$O (3 mL) at 60° C. with stirring. The solution was cooled down to 0° C. with stirring. The resulting crystals were collected and dried to yield the product (0.24 g). | Form 1 - Elemental Analysis: C 55.47; N 11.76; H 5.91 |
| 5. MeOH:H$_2$O = 7:3 | Compound A-TA (0.5 g) was dissolved in MeOH (7 mL) and H$_2$O (3 mL) at 60° C. with stirring. The solution was cooled | Form 1 - Elemental |

TABLE 3-continued

A Summary of Polymorph Formation Conditions for Compound A-TA.

| Solvents/Method | Synthesis/Crystallization | Polymorph Form |
|---|---|---|
| | down to RT with stirring. The resulting crystals were collected and dried to yield the product (0.32 g). | Analysis: C 55.23; N 12.00; H 5.86 |
| 6. acetone:$H_2O$ = 1:1 | Freebase (1.0095 g, 2.0 mmol) was dissolved in acetone (5 mL) and $H_2O$ (5 mL) at 45° C. with stirring. Then L-(+) tartaric acid (0.3121 g, 2.1 mmol) was added. The solution was cooled down to RT with stirring. Crystals appeared in 30 min. The resulting crystals were collected and dried to yield the product (1.1950 g, 85.7%). | Form 1 - Elemental Analysis: C 53.22; N 11.80; H 5.71 |
| 7. acetone:$H_2O$ = 4:6 | Freebase (1.0104 g, 2.0 mmol) was dissolved in acetone (6.5 mL) and $H_2O$ (10.5 mL) at 45° C. with stirring. Then L-(+) tartaric acid (0.3160 g, 2.1 mmol) was added. The solution was cooled down to RT with stirring. Crystals appeared in 60 min. The resulting crystals were collected and dried to yield the product (1.0581 g, 75.9%). | Elemental Analysis: C 53.18; N 11.63; H 5.71 |
| 8. acetone:$H_2O$ = 9:1 | Freebase (1.0174 g, 2.0 mmol) was dissolved in acetone (9 mL) and $H_2O$ (1 mL) at 45° C. with stirring. Then L-(+) tartaric acid (0.3142 g, 2.1 mmol) was added. The solution was cooled down to RT with stirring. Crystals appeared in 30 min. The resulting crystals were collected and dried to yield the product (1.2836 g, 92.1%). | Elemental Analysis: C 53.04; N 11.76; H 5.71 |

Dosage form selection: An oral immediate release capsule formulation is disclosed herein. One embodiment of this is a 25 mg/capsule (freebase equivalent) in a HPMC #2 capsule shell. Optionally, the drug loading can be increased by using a larger capsule so that each dosage unit can contain e.g. 50 mg/capsule or 100 mg/capsule (freebase equivalent).

Process selection: Compound A-TA is a drug substance associated with two molecules of water. To prevent dehydration that may occur during higher temperature of manufacturing process (such as drying process for wet granulation in tablet making), a direct mixing capsule fill manufacturing process is used. To protect the stability of the pharmaceutical composition before and after capsule formation, processes including capsule filling and storage steps are preferably conducted under moderated conditions, e.g., at a temperature of less than about 30° C. and a relative humidity less than about 60% and preferably less than about 45%.

Excipient selection: The excipients used in Compound A-TA capsules are commonly used excipients and can be found in FDA's Inactive Ingredient Database (IID).

Physicochemical and Biological Properties

The drug substance freebase is a weakly basic compound with a pKa of approximately 5.3. The aqueous solubility of the freebase is pH dependent. It is almost insoluble at a higher pH and the solubility increases dramatically at lower pH. To enhance the absorption and bioavailability, a tartrate salt (Compound A-TA) was made to enhance the dissolution of the molecule in compositions intended for oral administration. Capsules containing Compound A-TA have demonstrated a good dissolution profile (>85% release at 30 minutes), and a bioavailability of 20%-39% was achieved in dog PK testing using HPMC capsules.

Example 4. Capsules Containing Compound A-TA Prepared by Wet Granulation

Compound A-TA drug product was prepared as a capsule for oral administration that contains 25 mg of the Compound A freebase, which is equivalent to 34.26 mg of its tartrate salt (Compound A-TA). The capsule also contains 32.00 mg Prosolv®SMCC50 (Silicified Microcrystalline Cellulose), 89.74 mg Prosolv®SMCC90 (Silicified Microcrystalline Cellulose), 3.20 mg Croscarmellose sodium (VIVASOL®), and 0.80 mg Sodium Stearyl Fumarate (PRUV®). The total content weight in one capsule is 160 mg. A size #2 HPMC capsule shell with light blue opaque cap and white opaque body wasused. The Compound A-TA capsule was packaged inside a High-Density Polyethylene (HDPE) bottle and capped with a Low-Density Polyethylene (LDPE) cap containing a molecular sieve.

Figure 9:
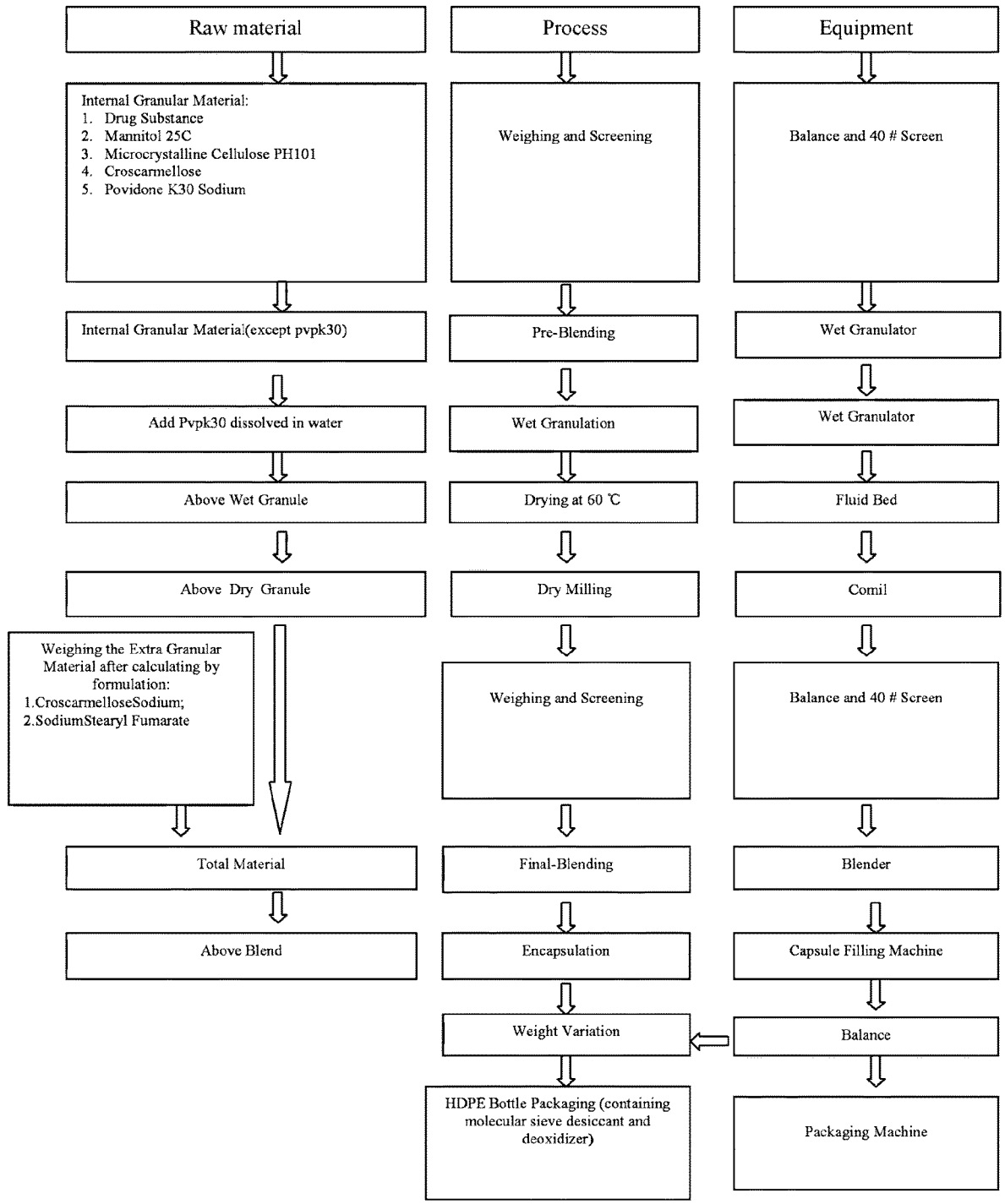
FIG. 9 is a process flow diagram for wet granulation process to prepare capsules filled with Compound A-TA.

A flow diagram summarizing the process is shown in FIG. 9.

TABLE 4

Materials for Wet Granulation Process.

| Category Of Excipients | | Function | Dosage/Capsule | Percentage/% |
|---|---|---|---|---|
| Internal Granular | Compound A-TA | API | 69.65 mg | 34.825 |
| | Mannitol 25 C | filler | 50 mg | 25 |
| | Microcrystalline Cellulose PH101 | filler | 60.35 mg | 30.175 |
| | Croscarmellose Sodium | disintegrant | 8 mg | 4 |
| | Povidone K30 | adhesive | 6 mg | 3 |
| Extra Granular | Croscarmellose Sodium | disintegrant | 2 mg | 1 |
| | Sodium Stearyl Fumarate | lubricant | 4 mg | 2 |
| | Weight Of Capsule Inclusion | | 200 mg | 100 |

The following steps were followed for wet granulation of Compound A-TA according to the list of ingredients in Table 4:

a. Weigh the internal granular materials (Compound A-TA, mannitol 25C, microcrystalline cellulose PH101), and screen through a 40 mesh sieve.

b. Mix internal granular material (excluding Povidone K30) in a wet granulator for 5-10 minutes to obtain mixture #1 in wet granulator.

c. Add Povidone PK30 dissolved in water to mixture #1 in wet granulator and process for 5-10 minutes to obtain mixture #2 d. Dry mixture #2 at about 60° C. in fluid bed for 30-60 minutes to obtain mixture #3.

e. Dry mill mixture #3 in comil for 10 minutes to obtain mixture #4.

f. Weigh the extra granular materials, croscarmellose sodium and sodium stearyl fumarate, and screen through a 40 mesh sieve. Add these to mixture #4 and mix for 10-20 minutes to obtain mixture #5.
g. Capsule fill with mixture #5, capsule shell was Vcap plus made of HPMC.
h. Package in a HDPE bottle (containing molecular sieve desiccant and deoxidizer).

Example 5. Preparation of Tablets Containing Compound A-TA Via Wet Granulation

Figure 10:
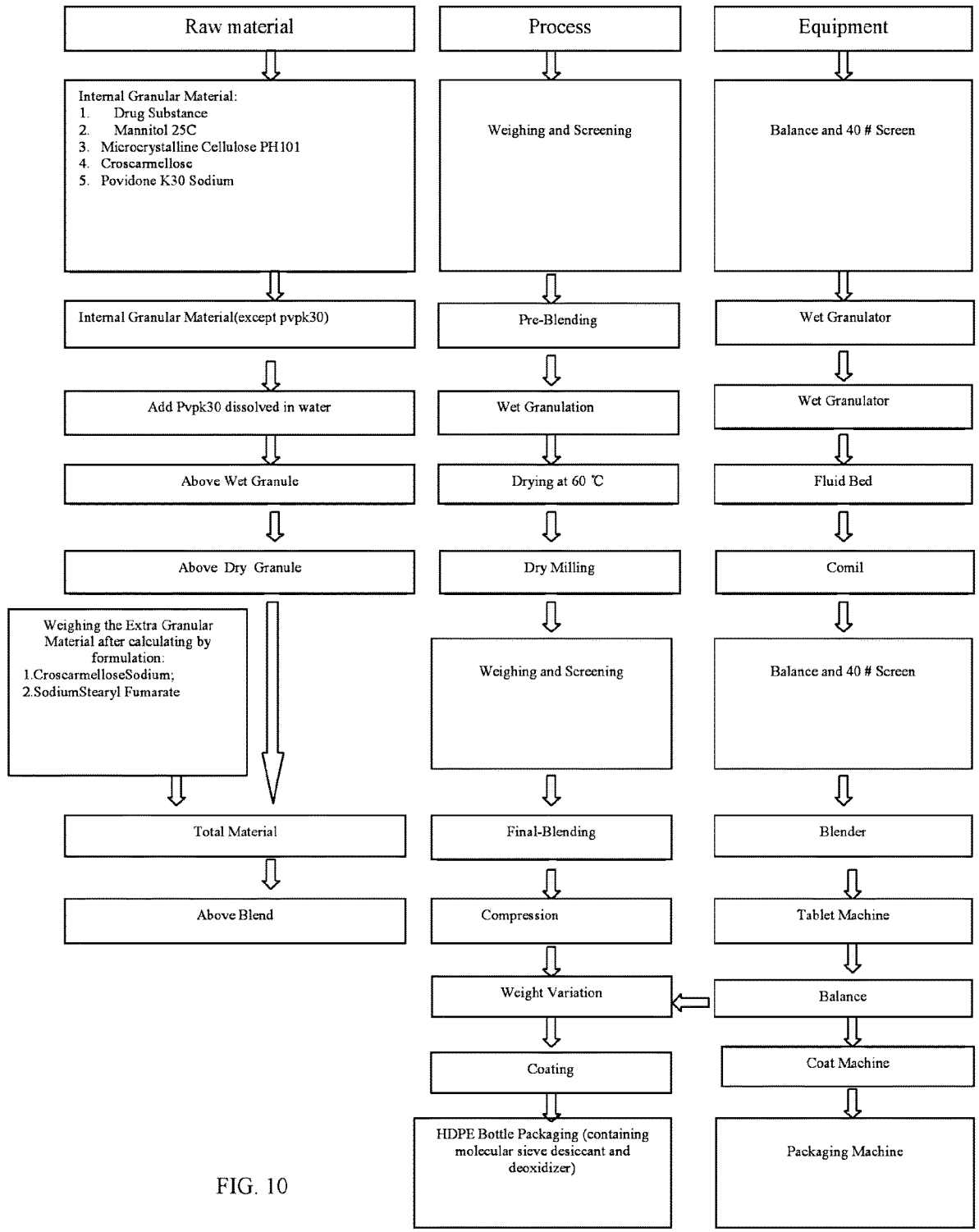
FIG. 10 is a process flow diagram for a wet granulation process to prepare tablets of Compound A-TA.

The same ingredients and proportions shown in Table 4 above were used to make tablets as dosage units of Compound A-TA by the following process steps:
a. Weigh the internal granular materials materials (Compound A-TA, mannitol 25C, microcrystalline cellulose PH101), and screen through a 40 mesh sieve.
b. Mix internal granular materials (except Povidone PK30) in a wet granulator for 5-10 minutes to obtain mixture #1 in the wet granulator.
c. Add PvpK30 dissolved in water to mixture #1 in wet granulator for 5-10 minutes to obtain mixture #2
d. Dry mixture #2 at about 60° C. in fluid bed for 30-60 minutes to obtain mixture #3.
e. Dry mill mixture #3 in comil for 10 minutes to obtain mixture #4.
f. Weigh the extra granular materials, croscarmellose sodium and sodium stearyl fumarate, and screen through a 40 mesh sieve. Add these to mixture #4 and mix for 10-20 minutes to obtain mixture #5
g. Compress mixture #5 in tablet machine, to obtain uncoated tablets #1.
h. Coat the tablets #1 with OPADRY 03B120001.
i. Package in a HDPE bottle (containing molecular sieve desiccant and deoxidizer). FIG. 10 shows a flow diagram of this process.

Example 6. Preparation of Capsules Containing Compound A-TA Via Direct Mixing

TABLE 5

Ingredients and Amounts Used to Prepare Capsules via Direct Mixing.

| Components | Function | Dosage | Percentage/% |
|---|---|---|---|
| Compound A-TA | API | 34.26 mg | 21.4 |
| Prosolv SMCC50 | Filler | 32.00 mg | 20.0 |
| Prosolv SMCC90 | Filler | 89.74 mg | 56.1 |
| Croscarmellose Sodium | Disintegrant | 3.20 mg | 2.0 |
| Sodium Stearyl Fumarate | Lubricant | 0.80 mg | 0.5 |
| Vcaps ® Plus, Size 2 | / | / | / |

Figure 11:
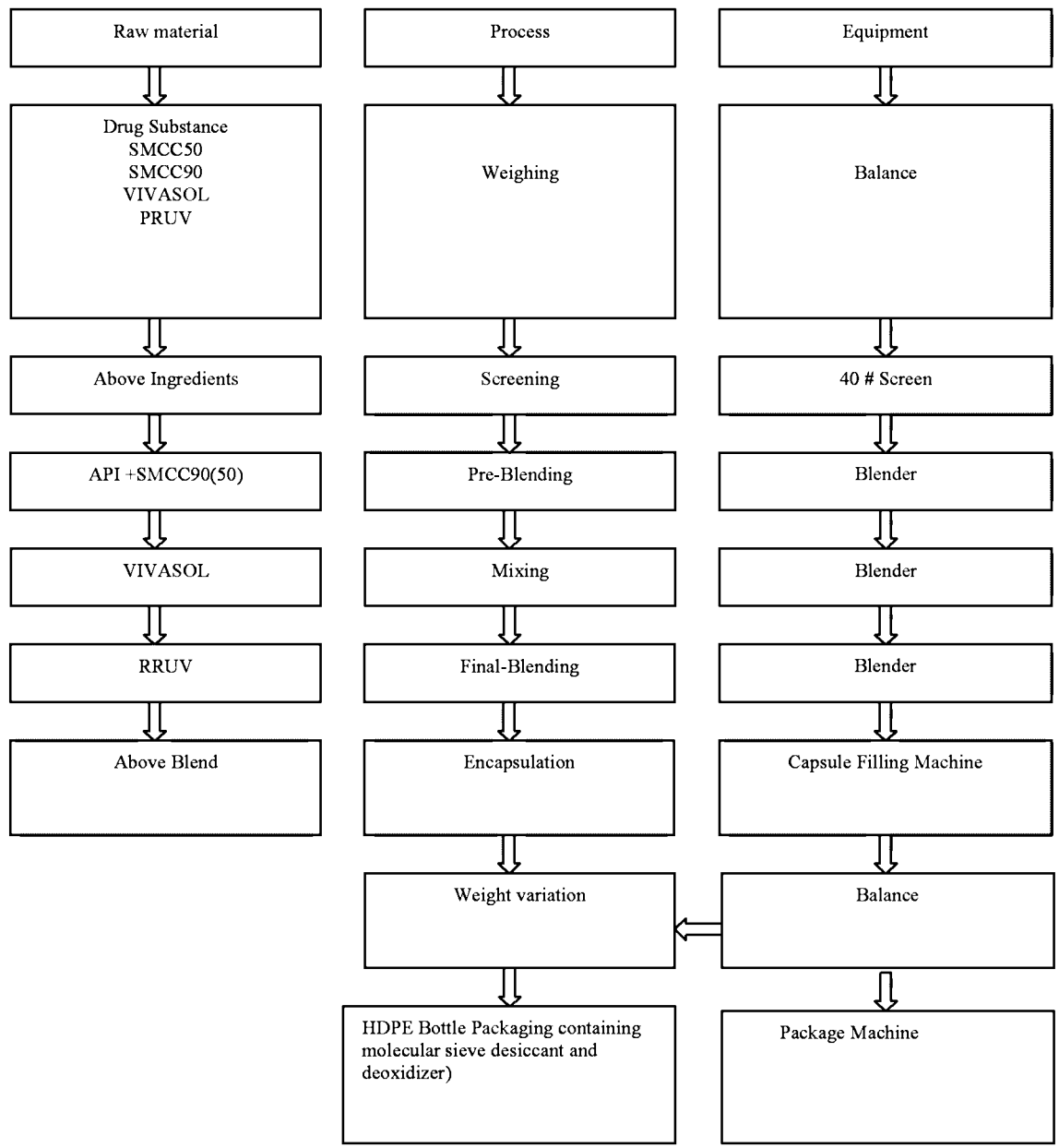
FIG. 11 is a process flow diagram for a direct mixing process to prepare capsules filled with Compound A-TA.

The excipients and material amounts for a different formulated product containing Compound A-TA are shown in Table 5. Using the materials in Table 5 and a direct mixing process, Capsules were prepared by the following steps:
a. Prepare and weigh the drug substance and all excipients
b. Mix Compound A-TA drug substance with SMCC90 and SMCC50. Sieve the blend through a 40 mesh sieve to obtain mixture #1.
c. Combine mixture #1 with croscarmellose sodium (Vivasol) and mix for 18-22 minutes to obtain mixture #2.
d. Sieve mixture #2 and sodium stearyl fumarate (Pruv) together, mixing for 3-7 minutes to obtain final granulated product e. Capsule fill
f. Package in a HDPE bottle
FIG. 11 provides a flow diagram of this process.

Example 7. Preparation of Tablets Containing Compound A-TA Via Direct Mixing

Figure 12:
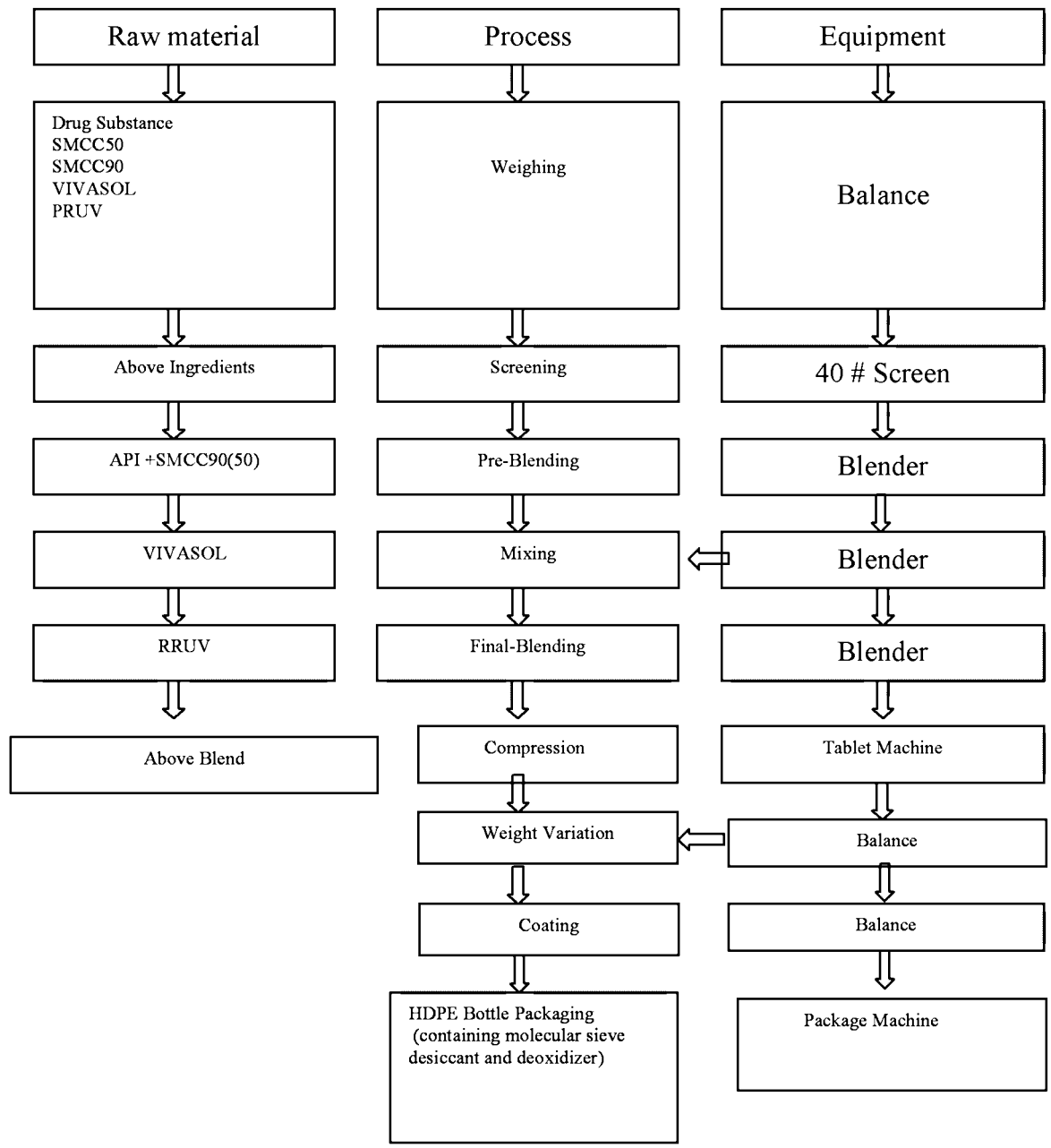
FIG. 12 is a process flow diagram for a direct mixing process to prepare tablets of Compound A-TA.

The excipients and material amounts shown in Table 5 were used to produce tablets using the following steps:
(a) Preparation and weighing of the drug substance and all excipients.
(b) Mix Compound A-TA drug substance and SMCC90, SMCC50. Sieve the blend through a 40 mesh sieve to obtain mixture #1.
(c) Combine mixture #1 with croscarmellose sodium (Vivasol) and mix for 18-22 minutes to obtain mixture #2.
(d) Sieve mixture #2 and sodium stearyl fumarate (Pruv) together, mix 3-7 minutes to obtain final granulate.
(e) Compress in tablet machine to obtain uncoated tablets #1.
(f) Coat the tablets #1 with OPADRY 03B120001.
Package in a HDPE bottle (containing molecular sieve desiccant and deoxidizer).
FIG. 12 provides a flow diagram of this process.

The invention claimed is:
1. A solid form of a L-(+)-tartrate salt of Compound A:

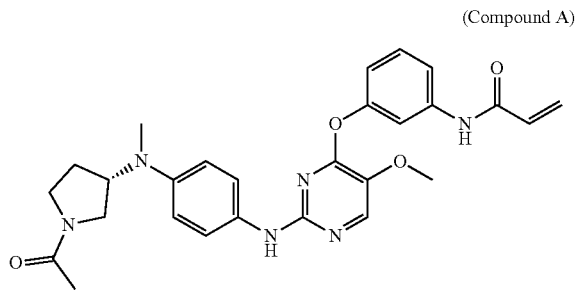 [SMILES: C=CC(=O)Nc1cccc(Oc2nc(Nc3ccc(N(C)[C@H]4CCN(C(C)=O)C4)cc3)ncc2OC)c1]

(Compound A)

wherein the solid form is crystalline having an X-ray powder diffraction pattern which comprises at least two peaks selected from: about 5.7°, about 9.8°, about 11.6°, about 14.7°, about 15.4°, about 16.1°, about 17.1°, about 19.3°, about 23.9°, about 24.5°, and about 25.4°, in terms of 2-theta.

2. The solid form of claim 1, which is a 1:1 salt of Compound A and L-(+)-tartaric acid.

3. The solid form of claim 1, which is a hydrate of the L-(+)-tartrate salt of Compound A.

4. The solid form of claim 3, which is a dihydrate.

5. The solid form of claim 1, wherein the X-ray powder diffraction pattern comprises at least three peaks, wherein the peaks are selected from: about 5.7°, about 9.8°, about 11.6°, about 14.7°, about 15.4°, about 16.1°, about 17.1°, about 19.3°, about 23.9°, about 24.5°, and about 25.4° in terms of 2-theta.

6. The solid form of claim 1, having a differential scanning calorimetry (DSC) thermogram comprising an endothermic peak at about 74° C. or a thermogravimetric analysis (TGA) substantially as shown in FIG. 7.

7. A pharmaceutical composition comprising the solid form of a L-(+)-tartrate salt of Compound A according to claim 1 and at least one pharmaceutically acceptable excipient.

8. The pharmaceutical composition of claim 7, which comprises at least two pharmaceutically acceptable excipients.

9. The pharmaceutical composition of claim 7, wherein the at least one pharmaceutically acceptable excipient is selected from a filler, a disintegrant, a glidant, an adhesive, a lubricant, and an antioxidant.

10. A dosage unit comprising a solid form of a L-(+)-tartrate salt of Compound A according to claim 1, in an amount equivalent to a weight of the free base of Compound A, selected from 25 mg, 50 mg, 75 mg, 100 mg, 150 mg, 200 mg, 250 mg, 300 mg, and 400 mg.

11. The dosage unit of claim 10, which is a tablet or a capsule.

12. The dosage unit of claim 10, which comprises at least one pharmaceutically acceptable excipient selected from silicified microcrystallinecellulose 50, silicified microcrystallinecellulose 90, pregelatinized starch, mannitol, croscarmellose sodium, povidone, and sodium stearyl fumarate.

13. The dosage unit of claim 10, which comprises an antioxidant.

14. A packaged pharmaceutical product, which comprises a pharmaceutical composition comprising a solid form of a L-(+)-tartrate salt of Compound A

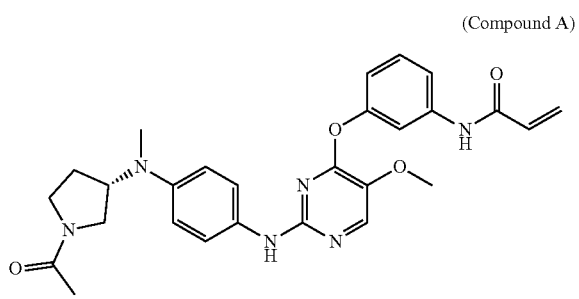 [SMILES: C=CC(=O)Nc1cccc(Oc2nc(Nc3ccc(N(C)[C@H]4CCN(C(C)=O)C4)cc3)ncc2OC)c1]

(Compound A)

wherein the solid form is crystalline having an X-ray powder diffraction pattern which comprises at least two peaks selected from: about 5.7°, about 9.8°, about 11.6°, about 14.7°, about 15.4°, about 16.1°, about 17.1°, about 19.3°, about 23.9°, about 24.5°, and about 25.4°, in terms of 2-theta, and a protective agent as two separate materials in a closed container.

15. A method to prepare a pharmaceutical composition according to claim 7, which comprises combining the solid form of a L-(+)-tartrate salt of Compound A with at least one pharmaceutically acceptable excipient.

16. A pharmaceutical composition comprising a solid form of a L-(+)-tartrate salt of Compound A:

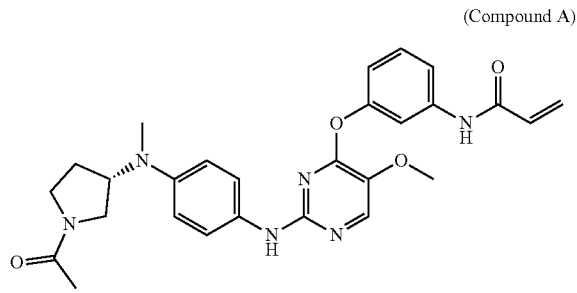 [SMILES: C=CC(=O)Nc1cccc(Oc2nc(Nc3ccc(N(C)[C@H]4CCN(C(C)=O)C4)cc3)ncc2OC)c1]

(Compound A)

wherein the solid form is crystalline having an X-ray powder diffraction pattern which comprises at least two peaks selected from: about 5.7°, about 9.8°, about 11.6°, about 14.7°, about 15.4°, about 16.1°, about 17.1°, about 19.3°, about 23.9°, about 24.5°, and about 25.4°, in terms of 2-theta, and wherein the solid form is a 1:1 salt of Compound A and L-(+)-tartaric acid, which is prepared by the method of claim 15.

17. A process for preparation of a solid form of a L-(+)-tartrate salt of Compound A

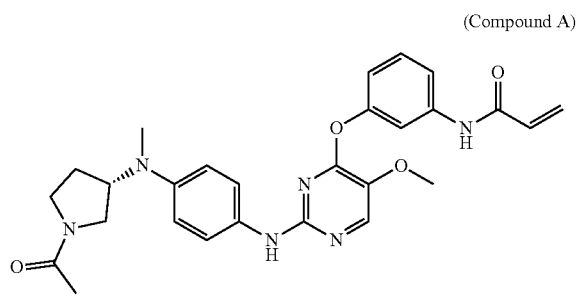 [SMILES: C=CC(=O)Nc1cccc(Oc2nc(Nc3ccc(N(C)[C@H]4CCN(C(C)=O)C4)cc3)ncc2OC)c1]

(Compound A)

wherein the solid form is crystalline having an X-ray powder diffraction pattern which comprises at least two peaks selected from: about 5.7°, about 9.8°, about 11.6°, about 14.7°, about 15.4°, about 16.1°, about 17.1°, about 19.3°, about 23.9°, about 24.5°, and about 25.4°, in terms of 2-theta, which comprises contacting Compound A with L-(+)-tartaric acid in the presence of a solvent.

18. A method to treat a condition selected from a proliferation disorder, a proliferative disorder, a tumor, an inflammatory disease, an autoimmune disease, psoriasis, dry eye, rheumatoid arthritis, or lupus in a subject, wherein the method comprises administering to a subject in need thereof a solid form of a L-(+)-tartrate salt of Compound A according to claim 1 or a pharmaceutical composition thereof.

* * * * *